United States Patent [19]

Kuliopulos et al.

[11] Patent Number: 5,648,244

[45] Date of Patent: Jul. 15, 1997

[54] PRODUCTION, PURIFICATION, CLEAVAGE AND USE OF FUSION PEPTIDES

[75] Inventors: Athan Kuliopulos, Cambridge; Christopher T. Walsh, West Newton, both of Mass.

[73] Assignee: President and Fellows of Harvard College, Cambridge, Mass.

[21] Appl. No.: 127,692

[22] Filed: Sep. 27, 1993

[51] Int. Cl.$^6$ .......................... C12N 15/09; C12N 15/63; C12N 15/70; C12N 15/62

[52] U.S. Cl. .................. 435/69.7; 435/71.1; 435/71.2; 435/172.3; 435/233; 435/320.1; 435/252.3; 435/252.33; 530/344; 935/10; 935/22; 935/23; 935/24; 935/27; 935/29; 935/38; 935/41; 935/47; 935/56; 935/72; 935/73

[58] Field of Search ...................... 435/69.7, 71.1, 435/71.2, 172.3, 233, 320.1, 252.3, 252.33; 530/344; 935/10, 22, 23, 24, 27, 29, 38, 41, 47, 56, 72, 73

[56] References Cited

U.S. PATENT DOCUMENTS

| | | | |
|---|---|---|---|
| 4,546,082 | 10/1985 | Kurjan et al. | 435/172.3 |
| 5,087,564 | 2/1992 | Mai et al. | 435/69.7 |

OTHER PUBLICATIONS

J. Pohlner et al., "A Plasmid System For High–Level Expression and In Vitro Processing of Recombinant Proteins", Gene 130:121–126, (Aug. 1993).

P. Markmeyer et al., "The pAX Plasmids: New Gene–Fusion Vectors for Sequencing, Mutagenesis and Expression of Proteins in *Escherichia colil*", Gene 93:129–134, (Sep. 1990).

C. Guan et al., "Vectors That Facilitate the Expression and Purification of Foreign Peptides in *Escherichia coli* by Fusion to Maltose–Binding Protein", Gene 67:21–30, (1988).

A. Kuliopulos et al., "N–Bromoacetyl–Peptide Substrate Affinity Labeling of Vitamin K Dependent Carboxylase", Biochemistry 31:9436–9444, (Oct. 1992).

J. W. Dubendorff et al., "Controlling Basal Expression in an Inducible T7 Expression System by Blocking the Target T7 Promoter With Iac Repressor", J. Mol. Biol. 219:45–59, (1991).

E. Hochuli et al., "Genetic Approach to Facilitate Purification of recombinant Proteins with a Novel Metal Chelate Adsorbent", Bio/Technology 6:1321–1325, (Nov. 1988).

H.M. Sassenfeld, "Engineering Proteins for Purification", Trends in Biotechnology 8:88–93, (Apr. 1990).

Kuliopulos, Athan et al., "Production, Purification, and Cleavage of Tandem Repeats of Recombinant Peptides," J. Am. Chem. Soc, 116:4599–4607 (1994).

Rieger, Andrea et al., "Restriction endonuclease ALw NI is blocked by overlapping Dcm methylation," Nucleic Acids Research, 21:4148 (1993).

Primary Examiner—Robert A. Wax
Assistant Examiner—Rebecca Prouty
Attorney, Agent, or Firm—Lyon & Lyon

[57] ABSTRACT

A method for producing a fusion peptide. A vector is provided with nucleic acid encoding a carrier peptide and at the 3' end of the nucleic acid, a unidirectional restriction endonuclease cleavage site recognized by a restriction endonuclease with the ability to create a non-palindromic 3-base overhang. The vector is cleaved with the restriction endonuclease to produce a cleaved vector. One or more nucleic acids encoding a desired peptide and having at least a 3-base overhang at each end configured and arranged for ligation with the cleaved vector is then ligated to the cleavage site.

44 Claims, 7 Drawing Sheets

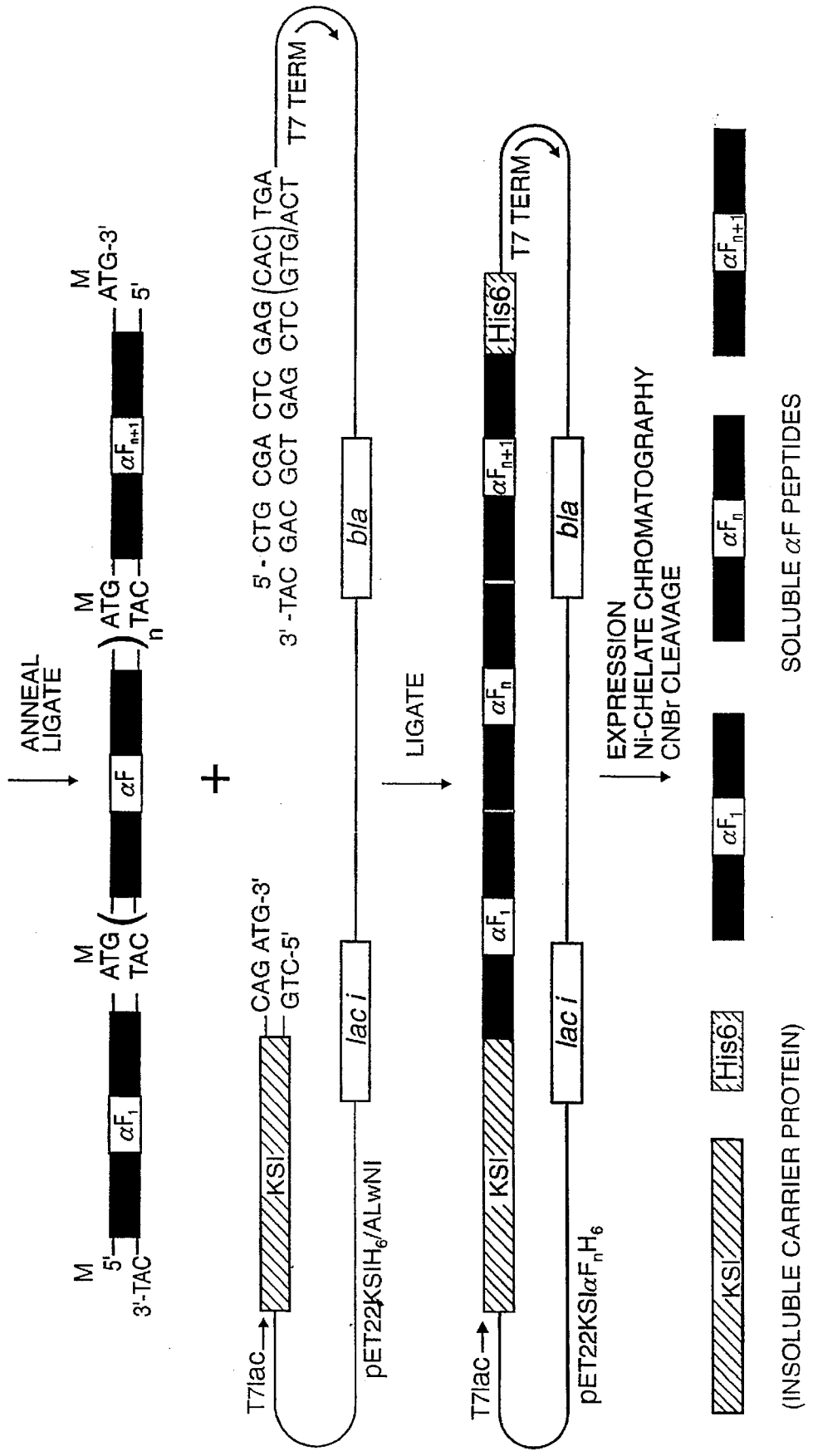

PRODUCTION, PURIFICATION, CLEAVAGE AND USE OF FUSION PEPTIDES

This invention was made with Government support under NIH Grant No. HL42443. The Government has certain rights to the invention.

FIELD OF THE INVENTION

The present invention relates to the production of fusion peptides that can be purified, cleaved into their constituent parts, and coupled to other compounds.

BACKGROUND OF THE INVENTION

To date, various methods for producing, purifying, cleaving and using fusion peptides have been explored or reported. These methods are described in some detail below, however, none of this discussion is admitted to represent prior art to the pending claims.

Production

The expression of the synthetic somatostatin gene as a fusion protein in *Escherichia coli* ("*E. coli*") is described in Itakura et al., *Science*, 198:1056–1063 (1977). A number of other recombinant proteins have also been produced as fusion proteins in *E. coli*, e.g. insulin A and B chain, calcitonin, β-endorphin, urogastrone, β-globin, myoglobin, human growth hormone, and angiotensin. Uhlen and Moks, "Gene Fusions for Purposes of Expression, An Introduction" in *Meths. in Enz.*, 185:129–143 (Academic Press, Inc. 1990).

Shen, "Multiple Joined Genes Prevent Product Degradation in *Escherichia Coli*" in *Proc. Natl. Acad. Sci. USA*, 81:4627–4631, 1984 and Shen et al., Canadian Patent No. 1,213,537, describe a method that allows the expression of a stable human proinsulin product in *E. coli* as encoded by a fused gene construction. Multiple, tandemly linked human proinsulin coding sequences were joined to the 3' side of a fragment containing the lac promoter and the coding sequence for a small part of the $NH_2$ terminus of β-galactosidase. The polypeptide product of a multiple copy proinsulin gene was then cleaved by a cyanogen bromide treatment into single proinsulin analog moieties having the extra C-terminal pentapeptide Arg-Arg-Asn-Ser-homoserine.

Lennick et al., "High-level expression of α-human atrial natriuretic peptide from multiple joined genes in *Escherichia coli*" in *Gene*, 61:103–112 (1987), describes a method which allows α-human atrial natriuretic peptide to be synthesized in stable form in *E. coli*. Eight copies of the synthetic α-hANP gene were linked in tandem, separated by codons specifying a four amino acid linker with lysine residues flanking the authentic N and C-termini of the 28 amino acid hormone. That sequence was then joined to the 3' end of the fragment containing the lac promoter and the leader sequence coding for the first seven N terminal amino acids of β-galactosidase. The expressed multidomain protein accumulated intracellularly into stable inclusion bodies and was purified by urea extraction of the insoluble cell fraction. The purified protein was cleaved into monomers by digestion with endoproteinase lys-C and trimmed to expose the authentic C-terminus by digestion with carboxypeptidase-B.

Kempe et al., "Multiple-copy genes: production and modification of monomeric peptides from large multimeric fusion proteins", in *Gene*, 39:239–245 (1985), describes a vector system designed for obtaining polypeptides synthesized in *E. coli*. Multiple copies of a synthetic gene encoding the neural peptide substance P(SP)(Arg-Pro-Lys-Pro-Gln-Gln-Phe-Phe-Gly-Leu-Met-$NH_2$) were linked and fused to the lacZ gene. Each copy of the SP gene was flanked by codons for methionine to create sites for cleavage by cyanogen bromide. The isolated multimeric SP fusion protein was converted to monomers of SP analog each containing carboxyl terminal homoserine lactone residue upon treatment with cyanogen bromide in formic acid. The homoserine lactone moiety was subjected to chemical modifications to produce a SP homoserine amide.

Purification

Metal affinity chromatography has recently been used as a basis for protein separations. Arnold, "Metal Affinity Separations: A New Dimension In Protein Processing" in *Bio/Technology*, 9:151–156 (1991).

Smith et al., "Chelating Peptide-immobilized Metal Ion Affinity Chromatography" in *J. Biol. Chem.*, 263:7211–7215 (1988) describes a specific metal chelating peptide on the $NH_2$ terminus of a protein that can be used to purify that protein using immobilized metal ion affinity chromatography. Recombinant fusions consisting of trpLE'-proinsulin or LHRH analogs were cleaved with cyanogen bromide thus exposing a N-terminal His-Trp Ni-affinity tag which was used to purify the smaller peptide hormones in 7M urea.

Hochuli et al., "Genetic Approach to Facilitate Purification of Recombinant Proteins With A Novel Metal Chelate Adsorbent", in *Bio/Technology*, 11:1321–1325 (1988), describe a polyhistidine peptide containing 2–6 adjacent histidines fused to mouse dihydropholate reductase at both the C and N-termini. The fusion proteins were purified on Ni(II)-NTA and subsequently treated with carboxypeptidase A to remove the polyhistidine tail. Fusion protein with the 6 histidine tail was extracted from *E. coli* with 6M GuHCl and loaded without further purification on a Ni(II)-NTA column.

Cleavage

Several chemical and enzymatic agents have been used to specifically cleave fusion proteins including cyanogen bromide, formic acid, hydroxylamine, collagenase, enterokinase factor $X_A$, thrombin, trypsin, clostripain and ala-subtilisin. Uhlen and Moks, *Meths. in Enz.*, 185:129–143 (1990) and Emtage, "Biotechnology & Protein Production" in *Delivery Systems for Peptide Drugs*, pp. 23–33 (1986).

Use

Kempe et al., "Multiple-copy genes: production and modification of monomeric peptides from large multimeric fusion proteins", in *Gene*, 39:239–245 (1985), describes the production of a SP peptide homoserine amide. A SP analog containing a carboxyl terminal homoserine lactone residue was treated with 30% $NH_4OH$ at room temperature for 30 minutes and also with methanolic $NH_3$ (10%).

Horn et al., *FEBS Letters*, 36:285–288 (1973) and Horn, *Analytical Biochemistry*, 69:583–589 (1975) describe a procedure for attaching cyanogen bromide peptides to resins by their C-terminal homoserine residues. The method involves lactonization of the homoserine residue with trifluoroacetic acid and subsequent aminolysis of the lactone with an amino resin.

Calloway et al., *Antimicrobial Agents and Chemotherapy*, 37:1614–1619 (1993) describes the production of cecropin A with a C-terminal homoserine that was chemically modified to produce a recombinant peptide with similar activity to that of cecropin A produced by cecropia pupae.

SUMMARY OF THE INVENTION

The present invention provides methods for producing fusion peptides that can be purified, cleaved into their constituent parts, and coupled to other compounds. More specifically, the invention concerns the tandem gene production of fusion peptides that can be purified using a metal affinity separation, cleaved with a chemical or enzyme, and coupled to a compound containing a nucleophile.

The present invention uses a vector to make these peptides. There are at least two features that make this vector useful. First, the vector encodes a large insoluble carrier peptide so that the fusion peptide product may be easily purified. This carrier peptide may then be cleaved (using cleaving agents well known in the art) from the fusion peptide product to yield large amounts of the pure desired peptide.

Second, the vector encodes a cleavage site that can be recognized by any restriction endonuclease with the ability to create a non-palindromic 3-base overhang. Those of ordinary skill in the art will recognize that several such restriction endonucleases are commercially available. Thus, the fusion peptide product will contain multiple copies of the desired peptide separated from each other by a single amino acid.

This single amino acid can then be cleaved with a specific chemical or enzyme to yield large amounts of the pure desired peptide. Those of ordinary skill in the art will recognize that these chemicals and enzymes may be, but are not limited to cyanogen bromide, formic acid, hydroxylamine, N-bromo succinimide, O-iodosobenzoic acid, collagenase, enterokinase factor $X_A$, thrombin, trypsin, clostripain and ala-subtilisin. Therefore, any desired peptide may be produced using any one of several restriction endonucleases along with the specific cleaving agent appropriate for the 3-base overhang created by the restriction endonuclease.

Thus, in one aspect the invention features a method for producing a fusion peptide. In this method, a vector having nucleic acid encoding a carrier peptide is provided. The vector also has (at the 3' end of the nucleic acid) a unidirectional restriction endonuclease cleavage site recognized by a restriction endonuclease with the ability to create a non-palindromic 3-base overhang. The vector is cleaved with the restriction endonuclease to produce a cleaved vector. One or more nucleic acids encoding a desired peptide and having at least a 3-base overhang at each end configured and arranged for ligation with the cleaved vector is then ligated to the cleavage site.

The term "peptide" refers to a compound formed of two or more amino acids joined together by a peptide bond. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan). Generally at least 5–50 amino acids are joined to form a polypeptide. A "fusion" is a combination of two or more subparts and thus a "fusion peptide" is a combination of two or more peptides.

The term "vector" refers to a replicating DNA molecule that can accept an inserted DNA segment from a foreign host cell. Examples of vectors include plasmids, phages, cosmids, phosmids, and bacteria.

The term "nucleic acid" refers to single- or double-stranded natural polymers in which bases (purines or pyrimidines) are attached to a sugar phosphate backbone. The term "carrier peptide" refers to a peptide that acts to support or stabilize a desired peptide or some other active ingredient.

A "cleavage site" (or ligation site) is a sequence of nucleic acids in a vector that when recognized by a restriction endonuclease will open by splitting its double-stranded nucleic acid and accept foreign DNA that is complimentary to the split strands. A cleavage site is "unidirectional" if a restriction endonuclease will recognize the cleavage site by reading it in only one direction, either 3' to 5' or 5' to 3', but not in both directions.

The term "restriction endonuclease" refers to any one of the many enzymes that cleave foreign DNA molecules at specific recognition sites. An "overhang" is one of the single strands created when a restriction endonuclease recognizes a cleavage site. The overhang is "non-palindromic" if the sequence of base pairs does not read the same (5' to 3') on complementary strands.

A vector is "cleaved" when one or more phosphodiester bonds between nucleotides in the vector is broken. The term "ligation" refers to the formation of a phosphodiester bond to join adjacent unbonded nucleotides. A "base" is a single nucleic acid subunit and three bases will encode a single amino acid.

In preferred embodiments, the fusion peptide is produced in E. coli., e.g., protease deficient E. coli, such as the strain BL21(DE3)pLysS from Novagen (catalogue No. 69388-1); the vector has a tightly controlled promoter, such as T7 lac located at the 5' end of the gene encoding the carrier peptide; the carrier peptide is insoluble, such as the first 125 amino acids of the ketosteroid isomerase ("KSI") gene; the single amino acid is methionine, the three base overhang is a 3' ATG overhang, the restriction endonuclease is AlwNI; and the desired peptide is either α-Factor peptide or FIXQS.

In other preferred embodiments, the ligation is performed in a single step; the desired peptide is produced in yields of at least 5 mg/L; a tag such as a $His_6$ tag is attached to the fusion peptide, the fusion peptide is separated using a metal affinity separation such as Ni-chelate chromatography and the fusion peptide is cleaved from the tag and carrier peptide with, for example, cyanogen bromide.

The term "protease" refers to an enzyme that digests proteins.

The T7 lac promoter is comprised of the T7 RNA polymerase promoter, the lac operator, and the lac repressor gene sequence in tandem. Studier, J. Mol. Biol., 219:45–59 (1991).

A carrier peptide is "insoluble" when less than 5 mg of protein dissolve in 100 mL of solvent. The extremely hydrophobic KSI protein is essentially insoluble in a water solvent and even in a solvent containing up to 40% acetonitrile/60% water. Even though the carrier peptide is insoluble in preferred embodiments, those of ordinary skill in the art will understand that soluble carrier peptides may also be used in the present invention.

Any desired peptide may be produced using the present invention including the α-Factor peptide and the FIXQS peptide. The mature α-Factor peptide is a 13 amino acid pheromone secreted by type MATa yeast cells (Elion et al., Cell, 60:649–664 (1990)) and the FIXQS sequence is a hydrophilic peptide encoding the highly soluble Gla domain of profactor IX (Kuliopulos et al., Biochemistry, 31:9436–9444 (1992)).

Several commercially available restriction endonucleases have the ability to create a non-palindromic 3-base overhang. For example, the restriction endonuclease AlwN I (New England Biolabs #514L) recognizes CAGNNN↓CTG (FIG. 1B), where N=C, A, T, or G. Therefore, the tandem gene linker sequences can be trimmed down to any single non-palindromic codon, thus preventing any frame shift potentially created by using 1, 2, 4, or 5 base overhangs generated by other commercially available restriction endonucleases. Blunt-end digestion (0-base overhang) will not allow for unidirectional ligation.

Since the 3-base overhang may be read in frame, a single ligation step will form all the DNA multimers (FIG. 1A) required for subsequent creation of many differently sized fusion peptides. These recombinant peptides can be produced and purified at yields of at least 50 mg/L of *E. coli* (Table 1). The high gene expression levels of the present invention may result from the combination of the carrier protein KSI, expression in the protease deficient *E. coli* strain BL21(DE3)pLysS, and the use of the very tightly controlled promoter in the pET22 vector system (Studier, *J. Mol. Biol.*, 219:37–44 (1991)).

The desired peptide may be purified using techniques known to those of ordinary skill in the art including metal affinity chromatography (a technique generally described in Arnold, "Metal Affinity Separations: A New Dimension In Protein Processing" in *Bio/Technology*, 9:151–156 (1991). The term "affinity chromatography" refers to a technique for separating molecules by their affinity to bind ligands attached to an insoluble matrix, so that the bound molecules can subsequently be eluted in a relatively pure state. This technique involves attaching a tag to the fusion peptide, performing the chromatographic separation and cleaving the fusion peptide at each of the single interspersed amino acids thereby releasing the carrier peptide, the tag and the desired peptide or peptides. For example, if the desired peptides are separated by a methionine, the fusion peptide may be cleaved with cyanogen bromide. If the desired peptides are separated by a tryptophan, the fusion peptide may be cleaved with O-iodosobenzoic acid. Those of ordinary skill in the art will recognize that other specific cleaving agents may be used depending on what amino acid separates the desired peptides in the fusion peptide (Fontana and Gross in *Practical Protein Chemistry*, pp. 67–120 (John Wiley & Sons, 1986)).

In a second aspect, a vector is provided. The vector is made of nucleic acid encoding a carrier peptide and at the 3' end of the nucleic acid, a restriction endonuclease cleavage site that is recognized by a restriction endonuclease with the ability to create a non-palindromic 3-base overhang.

In preferred embodiments the vector has a tightly controlled promoter, preferably T7 lac located at the 5' end of the encoded carrier peptide; the carrier peptide is insoluble, such as the first 125 amino acids of the ketosteroid isomerase gene; and the three base overhang is a 3' ATG overhang, and the restriction endonuclease is AlwNI.

In a third aspect, a method for producing peptide conjugates is provided. The peptide conjugates are produced by providing a peptide with a C-terminal homoserine lactone species and coupling the peptide with a non-resin compound containing a nucleophile in the presence of N,N'-dimethylformamide ("DMF") and triethylamine ("Et$_3$N").

In preferred embodiments, the nucleophile is a primary amine or saturated ammonia in DMF, the primary amine is a chromophore or fluorophore, etc. is selected from the group of analogs of fluorescein, analogs of dansyl, and analogs of biotin, and is radioisotopically labelled.

In a fourth aspect a method for producing peptide conjugates under aqueous conditions is provided. The peptide conjugates are produced by providing a peptide with a C-terminal homoserine lactone species and coupling the peptide with a compound containing a primary amine under aqueous conditions.

In preferred embodiments the primary amine containing compound is an amino-alkyl Sepharose resin; the peptide is FIXQS; the peptide conjugate is used to generate a peptide affinity column uniquely tethered at the C-terminus suitable for affinity purification of vitamin K-dependant carboxylase; and the coupling is performed at pH 5 to 7.

In a fifth aspect, a vector is provided. The vector is made of nucleic acid encoding a recombinant fusion peptide having at least part of a ketosteroid isomerase gene linked to one or more desired peptides and a His$_6$ tag attached to a C-terminal desired peptide. Each desired peptide is separated from another by a single amino acid.

In preferred embodiments, the part of the ketosteroid isomerase gene is the first 125 amino acids of the ketosteroid isomerase gene. There is a tightly controlled promoter on the 5' end of the part of the ketosteroid isomerase gene, the promoter is T7 lac, the amino acid is methionine, the desired peptide is α-Factor or FIXQS.

The general usefulness of this invention is the inexpensive production of essentially unlimited quantities of peptides at very high purity for research and potentially for medicinal purposes. The present invention provides an efficient method for in frame unidirectional ligation by using a restriction endonuclease that is capable of recognizing a 3-base overhang. The flexibility of the present invention is demonstrated by the fact that any amino acid may be used to separate the desired peptides in the fusion peptide. The flexibility of the invention is further demonstrated by the fact that a large number of peptide-conjugates may be formed under a variety of conditions. Those of ordinary skill in the art will recognize that there are many advantages to using this inexpensive, flexible and efficient invention.

The fusion peptides produced by the present invention may contain novel mutants of naturally occurring peptides. These mutations include the replacement of the last naturally occurring amino acid with a homoserine lactone species and inserting any single amino acid between desired peptides.

Other features and advantages of the invention will be apparent from the following description of the preferred embodiments thereof and from the claims.

BRIEF DESCRIPTION OF THE DRAWINGS

FIG. 1A–1D diagram a strategy for the construction, production, Ni-chelate purification, and cyanogen bromide cleavage of ketosteroid isomerase-tandem peptide-His$_6$ fusion proteins.

FIG. 1A diagrams oligonucleotides encoding both strands of the 13 amino acid α-Factor peptide that were annealed, phosphorylated, and unidirectionally self-ligated to form an array of tandem repeats of α-Factor-encoding units (αF$_n$) separated by ATG codons. These multimers were then ligated into the AlwN I site of the parent vector depicted in FIG. 1B to create KSI-αF$_n$-His$_6$ fusion genes where n=0 to 13.

FIG. 1B diagrams the pET22KSIH$_6$ parent vector containing a unique AlwN I site suitable for unidirectional ligation of duplex DNA multimers terminating in ATG-3' and 3'-TAC single-stranded DNA overhangs.

FIG. 1C diagrams the pET22KFMH vector containing the KSI-FIXQS-M-H$_6$ fusion gene that was used to produce the FIXQS-homoserine-lactone 60 amino acid peptide. A methionine residue was placed upstream of the His$_6$ cassette to allow cyanogen bromide cleavage of the His$_6$ tag away from the 60 amino acid peptide after purification by Ni-chelate chromatography.

FIG. 1D diagrams the pET22KFH vector containing the KSI-FIXQS-H$_6$ fusion gene that was used to produce the FIXQS-H₆ 67 amino acid peptide. The C terminal His₆ was designed to remain attached to the FIXQS peptide after cyanogen bromide cleavage.

FIG. 3A depicts reverse-phase HPLC of α-Factor cyanogen bromide cleavage products. The cyanogen bromide reaction mixture was extracted with 60% H₂O/40% CH₃CN/ 0.1% TFA and injected onto a 4×250 ml Vydac RP-HPLC column and a linear gradient (0%+5%/min for 5 min and then 1%/min for 25 min) of acetonitrile/0.1% trifluoroacetic acid (TFA) in distilled deionized water/0.1% TFA was employed. Peptide peaks were detected by UV absorbance at 214 nm. The composition of each of the indicated peaks was verified by FAB-MS. The UV absorption spectra of each of the indicated HPLC peaks is shown to the right.

FIG. 3B depicts the same as in FIG. 3A except that the peptide was the recombinant 67 amino acid peptide FIX-QSH₆ peptide purified by Ni-chelate affinity chromatography.

DESCRIPTION OF THE PREFERRED EMBODIMENTS

Figure 1B:
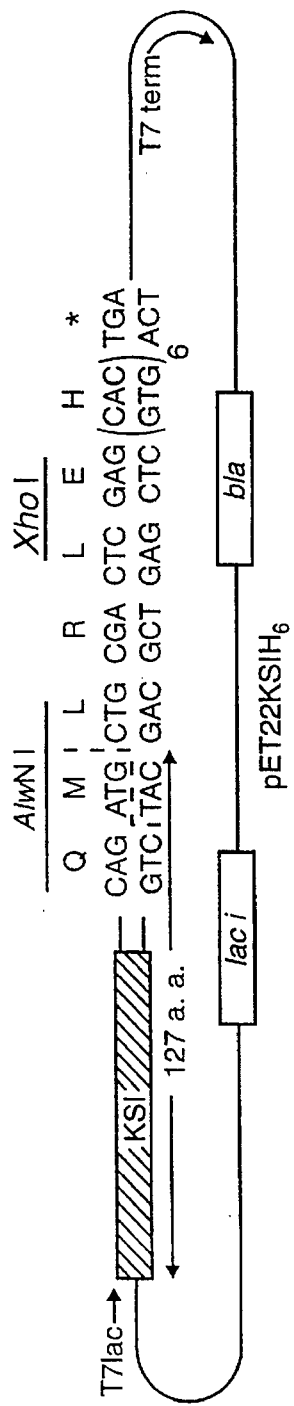

Preferred embodiments of the present invention are described in detail below, however, the following description of the preferred embodiments is not intended to limit in any way the scope of the present invention which is defined in the appended claims.

A method to produce fusion peptides containing a carrier peptide, desired peptides interspersed by single amino acid residues, and terminating in a tag is described below. The fusion peptides may be purified and cleaved into homogenous peptide units. The method involves providing a specifically designed vector. The vector encodes a carrier peptide that is large and insoluble thus allowing for easy purification of the fusion peptide product. The vector also encodes a cleavage site for a restriction endonuclease that is capable of producing a 3-base overhang. Thus, by choosing the appropriate restriction endonuclease, any amino acid may separate the desired peptides in the fusion peptide product. Then the appropriate cleaving agent may be selected to separate the carrier peptide, the single amino acids, and the desired peptides. Since the desired peptide terminates in a homoserine lactone species, it may be coupled to any nucleophile containing non-resin compound.

Carrier Peptide

The use of an insoluble carrier peptide aids in the purification of the fusion peptide product. For example, after cleavage the extremely hydrophobic KSI carrier protein is essentially insoluble even up to 40% acetonitrile-60% water (FIG. 1A). Those of ordinary skill in the art will recognize that many other carrier proteins may also be used, including soluble carrier proteins. Indeed, the present invention provides purification protocols tailored for each different recombinant peptide depending on its solubility in water. Thus, the crude α-Factor peptide is already 80% pure (FIG. 3) prior to further HPLC purification.

Those versed in the art of solid phase peptide synthesis are familiar with the problems of purification of peptides greater than 10 to 20 amino acids in length. In fact, a 60–67 amino acid peptide presents quite a challenging HPLC purification since the starting crude synthetic peptide mixture (only ca. 30% pure) has hundreds or thousands of closely migrating contaminants such as deletions of single amino acids which are sometimes impossible to purify away from the correct peptide.

Restriction Endonuclease

The use of a restriction endonuclease capable of recognizing a 3-base overhang allows for in frame unidirectional ligation. For example, the restriction endonuclease AlwN I can be used to cleave an expression vector to leave a single ATG 3' 3-base overhang suitable for accepting any duplex DNA with a 3' TAC overhang and a 5' ATG overhang. Thus, a single ligation step will form multiple tandem copies of peptide encoding DNA. Those of ordinary skill in the art will recognize that several other restriction endonucleases are also capable of recognizing a 3-base overhang.

Those of ordinary skill in the art will also recognize that the restriction endonuclease should be selected to allow an amino acid that does not occur in the desired peptide to separate the desired peptides. For example, since the restriction endonuclease AlwN I can recognize a 3-base region encoding the relatively rare amino acids Met and Trp, a wide variety of peptides may be chosen as the desired peptides to be used with this particular restriction endonuclease.

Peptide Conjugates

The desired peptide may be coupled to a non-resin compound containing a nucleophile in the presence of DMF and ET₃N to produce a wide variety of useful compounds. While those of ordinary skill in the art will recognize that the desired peptide may be coupled to any non-resin compound containing a nucleophile, in preferred embodiments the non-resin compound is soluble, the nucleophile is a primary amine, saturated ammonia in DMF, a chromophore or a fluorophore, radioisotopically labelled, or selected from the group of analogs of fluorescein, analogs of dansyl, and analogs of biotin. Thus, peptide conjugates may be formed with a wide variety of nucleophile containing compounds in yields ranging from 50% to greater than 90% (Table 2, FIG. 4). This procedure employed anhydrous DMF with Et₃N as a base to achieve a simple reliable and widely applicable coupling system for the test peptide, since DMF serves as a universal solvent for most small to medium size peptides.

Figure 5:
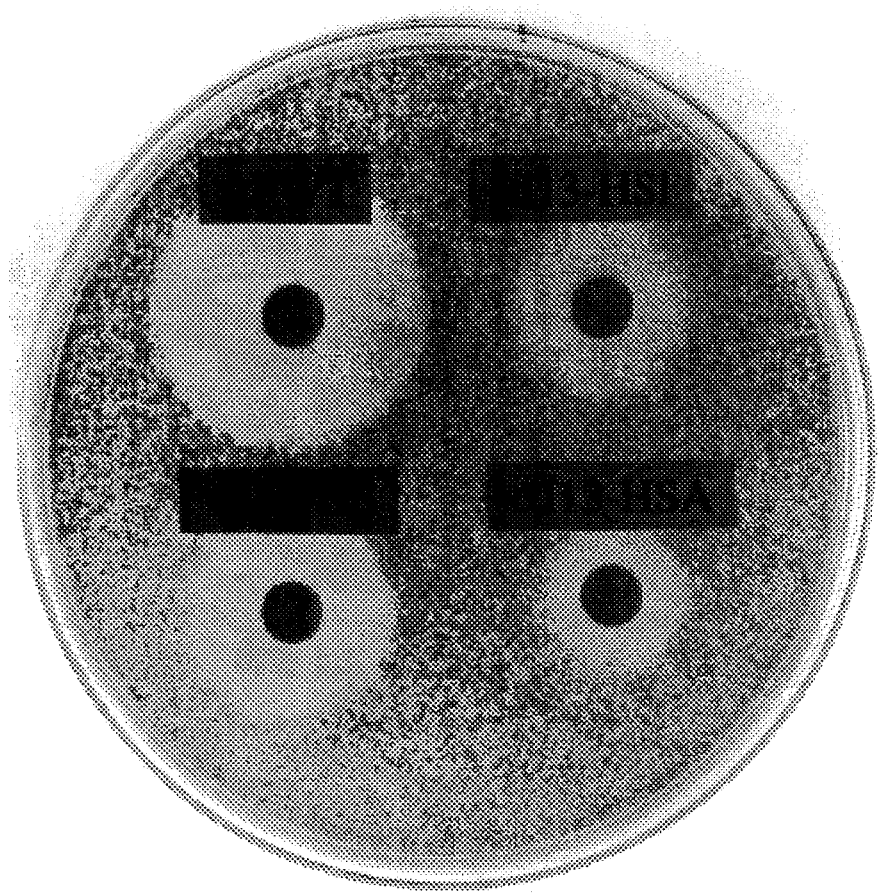
FIG. 5 depicts a copy of the growth in a petri dish of recombinant α-mating factor peptides. Lines of yeast MATa/ sst1Δ strain EY957 were grown on YPD plates. α-Factor peptides were dissolved in DMSO and spotted on sterile 6.5 mm paper disks. Peptide amounts were as follows: wild type α-Factor 595 pmol; α-I13-homoserine-lactone 6,850 pmol; α-I13-homoserine 1,130 pmol; and α-I13-homoserine-amide 2,820 pmol.

A total of seven different e factor peptide HS—NH—R compounds were synthesized, purified, characterized and tested for biological activity in an in vivo yeast cell cycle arrest assay (Table 2, FIG. 5). Some of the recombinant α-factor peptides had similar biological activity as wild type α-factor peptides. The coupling of both the α-factor peptide and the FIXQS peptide to a number of nucleophile containing non-resin compounds has demonstrated the biological utility of the HS lactone coupling chemistry.

The desired peptide may also be coupled to a primary amine containing compound under aqueous conditions. Thus, the present invention also has the ability to use a peptide HS lactone to make an affinity peptide column. The present invention may be used to couple under aqueous conditions the recombinant 59 amino acid HS lactone peptide FIXQS to an aminoalkyl sepharose resin in 93% yield to produce a peptide affinity column tethered at the C-terminal end. This column was successfully used to purify the membrane bound vitamin K dependent carboxylase ca.3000 fold.

EXAMPLES

This invention will be more fully understood with reference to the examples which follow. The following examples are intended to illustrate the invention, but not to limit its scope which is defined in the claims appended hereto. The following examples are presented to illustrate the advantages of the present invention and to assist one of ordinary skill in the art in making and using the same, but are not intended in any way to otherwise limit the scope of the disclosure or the protection granted by letters patent hereon.

In the following examples, the *E. coli* strain DH5αFIQ was from our laboratory; the BL21(DE3)pLysS strain was from Novagen; and all restriction endonucleases were from New England Biolabs.

Example 1

Strategy for the Production of α-Factor and FIXQS Peptides and Peptide Conjugates Tandem repeats of the 13 amino acid residue yeast α-mating factor (αF) were ligated into a pET vector downstream of the ketosteroid isomerase (KSI) gene and upstream of a $His_6$ cassette. A KSI-(αF)5-$His_6$ fusion was overproduced in *E. coli*, purified by Ni chelate chromatography, and then cleaved with cyanogen bromide to release insoluble KSI, the $His_6$ tail, and the α-factor peptide units each terminating with homoserine (HS) lactone. HPLC yielded pure peptide in a yield of 56 mg/L.

The α-factor-HS lactone could be ammonolyzed or hydrolyzed to yield α-factor-HS-amide or α-factor-HS, respectively. The α-factor-HS peptide had similar biological potency as authentic α-factor in yeast cell arrest assays. The α-factor-HS lactone was also reacted with a number of other compounds including analogs of fluorescein, dansyl, and biotin to produce α-factor peptides derivatized exclusively at the C-terminus.

To test the ability of the expression system to produce longer peptides, 60–67 amino acid peptides encoding the Gla domain of profactor IX (FIXQS, FIXQS-$His_6$) were also produced. Yields of 50–55 mg/L of pure FIXQS-$His_6$ and FIXQS-HS lactone were obtained. The FIXQS-HS lactone could be coupled to an amino-alkyl Sepharose resin to generate a peptide affinity column tethered uniquely at the C-terminus suitable for affinity purification of vitamin K-dependent carboxylase.

Example 2

Strategy for the construction and production of tandem repeats as fusion peptides in *E. coli*.

To enhance the stability of the 13 residue yeast α-mating factor test peptide, the peptide was produced as tandem repeated units attached to the highly expressed 375 base pair (125 amino acid) bacterial steroid isomerase gene and upstream of a $His_6$ cassette. The resulting fusion proteins were then purified from inclusion bodies by Ni-chelate chromatography under denaturing conditions, and digested with cyanogen bromide at junctional methionines releasing free α-Factor peptide units.

The overall strategy for construction and production of the α-Factor fusion proteins is shown in FIG. 1A. Complementary oligonucleotides encoding the α-Factor peptide were synthesized, annealed, and unidirectionally self-ligated using 3-base -ATG-3', 3'-TAC- overhangs to form a large array of tandem repeated α-Factor units separated by single methionine codons. The expression vector pET22KSIH$_6$ (FIG. 1B; H represents His) was digested with AlwN I which recognizes:

CAGNNN↓CTG. (SEQ. I.D. NO. 1)

The different size tandem repeated α-Factor units (αF$_n$) were then unidirectionally ligated into the pET22KSIH$_6$ AlwN I site to produce the final pET22KSIαF$_n$H$_6$ constructs (n=0 to 14) which could be tested for protein production levels.

Figure 1C:
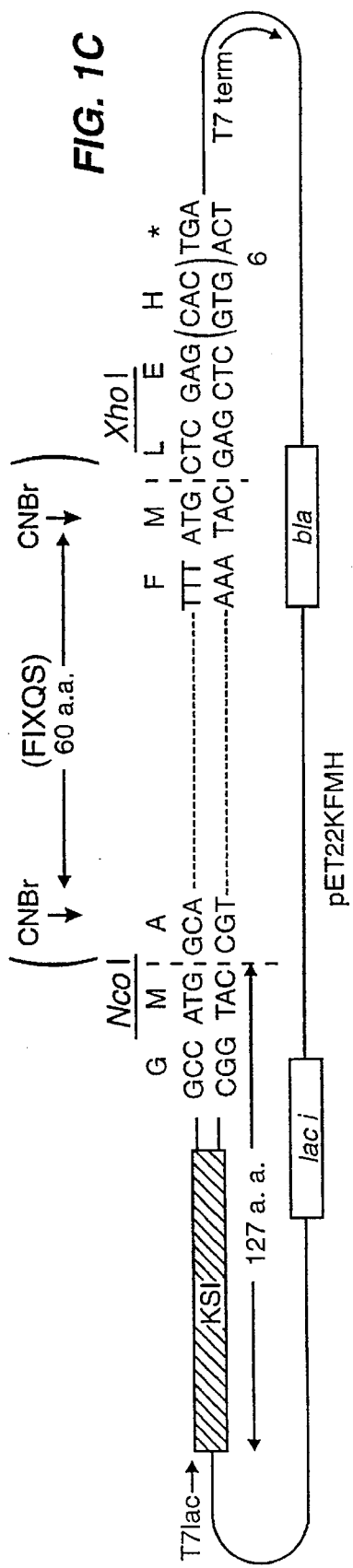
Figure 1D:
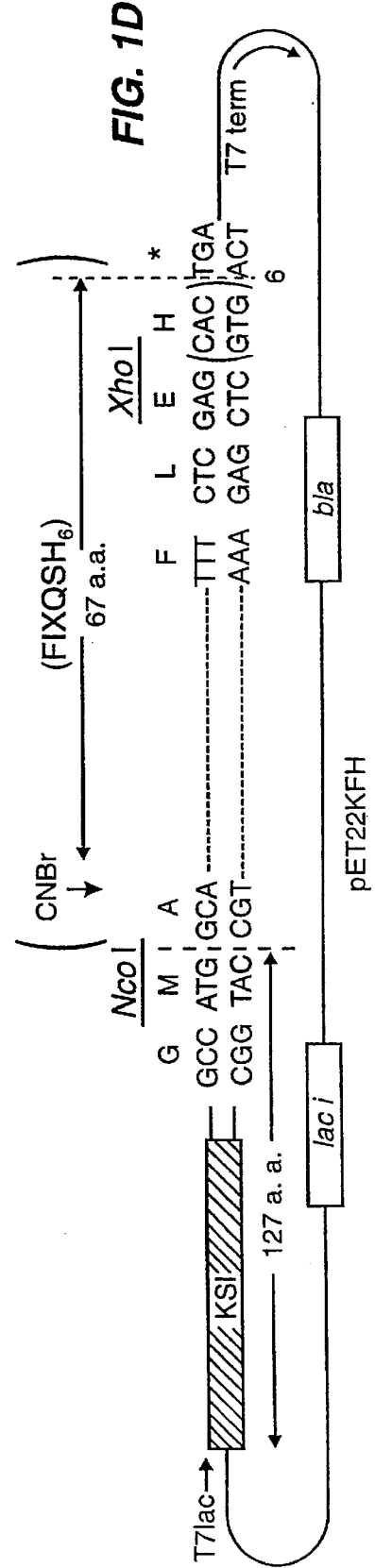

To test the ability of the expression system to produce longer peptides, 60–67 amino acid peptides encoding the highly soluble Gla domain of profactor IX (FIXQS, FIXQSH$_6$) were also constructed as KSI fusions (FIGS. 1C and 1D). Note that the FIXQS peptide is produced as a fusion protein, KSIFIXQSMH$_6$, which differs from the KSIFIXQSH$_6$ fusion by a single additional methionine residue placed just prior to the C-terminal His$_6$ tag. The His$_6$ remains attached to the FIXQSH$_6$ but not the FIXQSMH$_6$ peptide after cyanogen bromide cleavage.

Example 3

Figure 2:
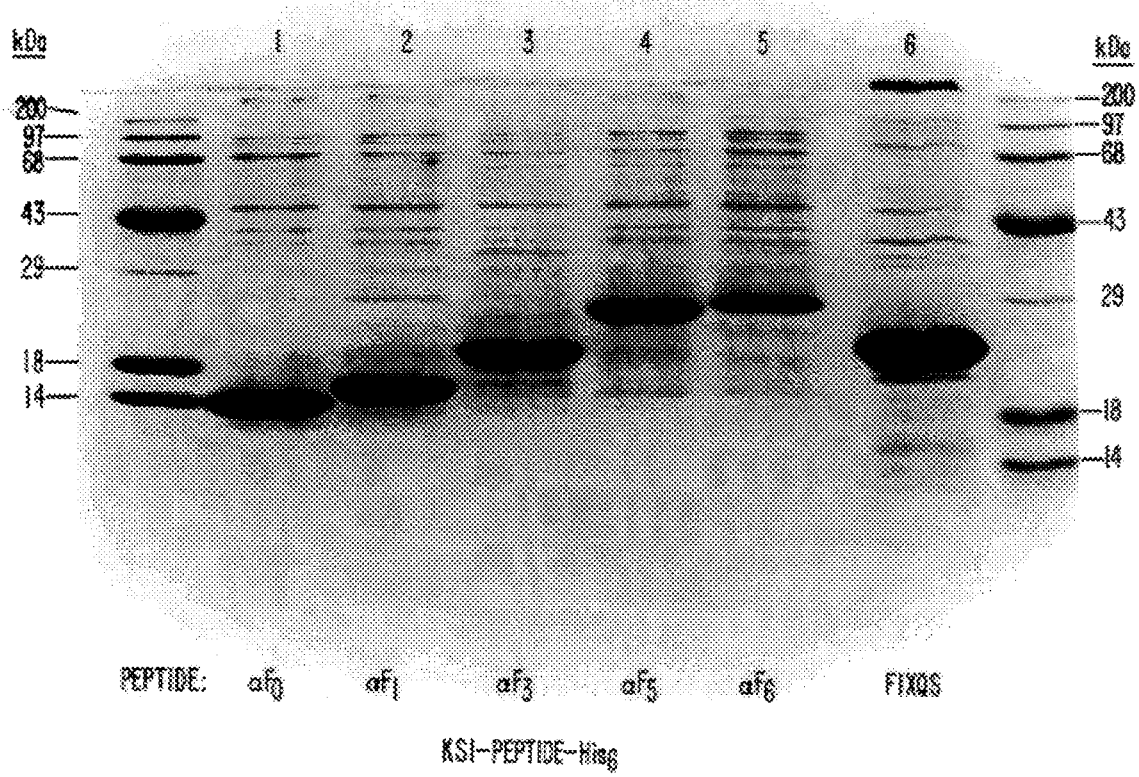
FIG. 2 diagrams a copy of the polyacrylamide gel for the KSI-αF$_n$-H₆ and KSI-FIXQS-M-H₆ fusion proteins that were produced in *E. coli* and analyzed by 15% SDS-polyacrylamide gels stained with Coomassie Blue R-250. Gel 1 lanes 1–5 are insoluble protein fractions from the KSI-αF$_n$-H₆ fusion constructs where n=0, 1, 3, 5, and 6. Molecular weights in kDa are shown on the left for Gel 1. Gel 2 lane 6 is the insoluble protein fraction from the KSI-FIXQS-M-H₆ fusion construct. Molecular weights in kDa are shown on the right for Gel 2.

Production and purification of recombinant α-Factor, FIXQS, and FIXQS-H$_6$ peptides Each of the different KSIαF$_n$H$_6$ and KSIFIXQS(M)H$_6$ constructs were expressed in the protease deficient strain BL21(DE3)pLysS under the tight control of the T7 lac promoter in the pET22 vector. The production levels are shown in FIG. 2 and the amounts of fusion protein as a percentage of total protein are given in Table 1. The KSIαF$_n$H$_6$ fusion proteins were processed into inclusion bodies and comprised the majority of the insoluble protein fraction as shown (FIG. 2).

The production levels of the KSIαF$_n$H$_6$ fusion proteins gradually decreased as n incremented from 0 (70% of total insoluble protein) to n=6 (55% of total insoluble protein). When n was >6 the production levels dramatically decreased and became <1% of total cellular protein at n≦11. Since, however, the peptide/KSI-peptide-H$_6$ mass ratio also increased from 0% (n=0) to 42% (n=6), the theoretical maximum yield of peptide occurred at n=5 (Table 1). Thus, when n=5 (5×14=70 a.a.), the α-factor peptide comprised 70 amino acids/206 amino acids or 37.3% (da/da) of the mass of the fusion polypeptide yielding the greatest amount of α-factor/L of *E. coli*.

The inclusion body protein pellets were solubilized in 6M guanidine-HCl and the KSI-peptide-H$_6$ fusion proteins were purified to homogeneity by Ni-chelation affinity chromatography under denaturing conditions as determined by Ag-stained SDS-PAGE gels. As shown in FIG. 2, Gel 1, lanes 1–5 are insoluble protein fractions from IPTG-induced *E. coli* BL21(DE3)pLysS harboring the pET22KSI-αF$_n$-H$_6$ fusion constructs where n=0, 1, 3, 5, and 6. Molecular weights in kDa are shown on the left for Gel 1. Gel 2, lane 6 shows the insoluble protein fraction from the KSI-FIXQS-M-H$_6$ fusion construct. Molecular weights in kDa are shown on the right for Gel 2.

Fusion proteins could also be purified from the soluble cellular fraction under native conditions but these Ni-chelate chromatography preparations were always contaminated with several minor proteins (ca. 5%) which co-eluted from the Ni resin at 300 mM imidazole The pure KSIαF$_5$H$_6$ protein purified in the presence of guanidine was then quantitatively cleaved by cyanogen bromide at the junctional methionines releasing KSI (1–112, 113–126), the His$_6$ tail, and the αF peptide units each terminating in a HS(lactone) residue.

Figure 3A:
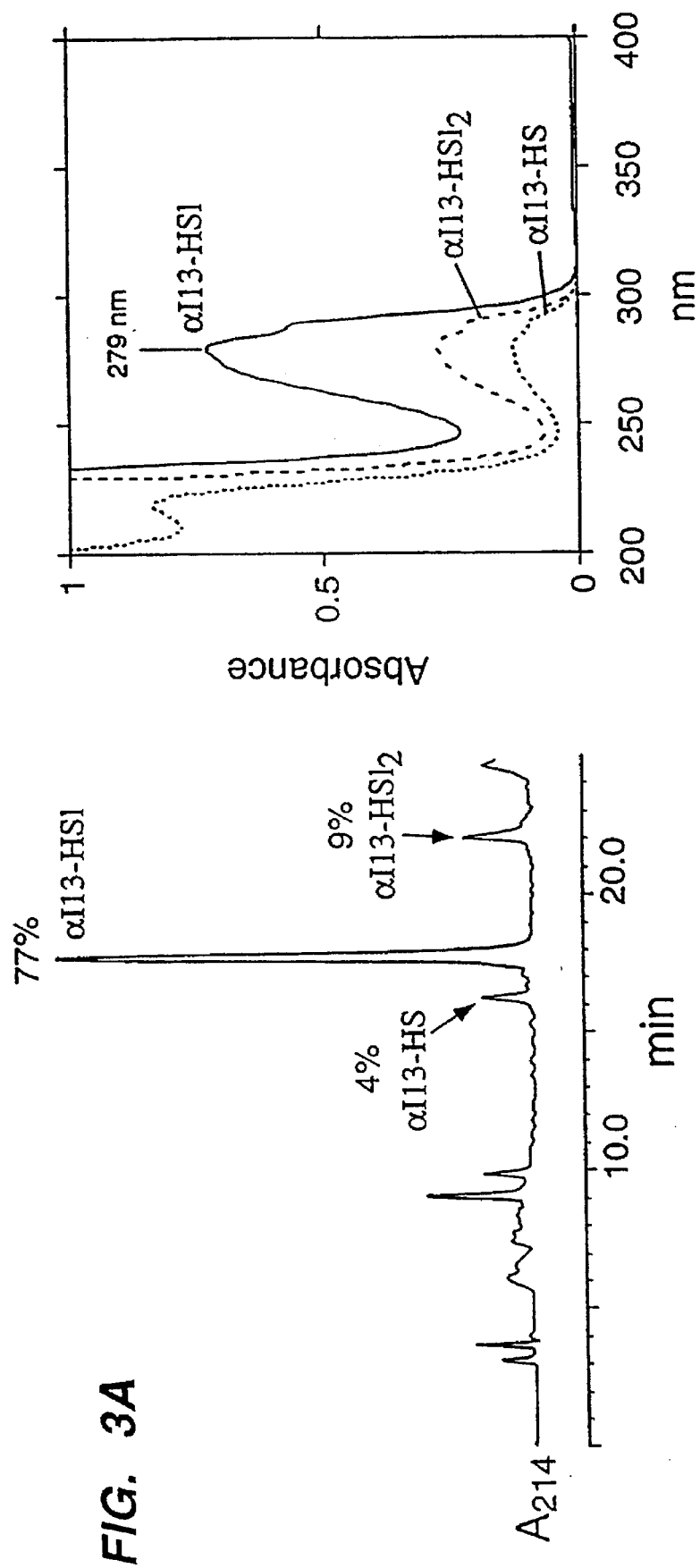
FIGS. 3A and 3B depict the determination of purity and composition of crude cyanogen bromide cleavage reaction mixtures of recombinant α-Factor and FIXQSH₆ peptides.

As shown in FIG. 3A, the αF peptides could be easily extracted away from extremely hydrophobic KSI peptides using 60% H$_2$O/40% CH$_3$CN/0.1% TFA and injected onto a 4×250 mm Vydac RP-HPLC column. A linear gradient (0% +5%/min for 5 min and then 1%/min for 25 min) of acetonitrile/0.1% trifluoroacetic acid (TFA) in distilled-deionized water/0.1% TFA was employed. Peptide peaks were detected by UV absorbance at 214 nm. Fractions containing the desired peptides were combined and lyophilized. Reinjection of purified peptides showed them to be >99% homogeneous. The composition of each of the indicated peaks was verified by FAB-MS. The UV absorption spectra of each of the indicated HPLC peaks is shown to the right. The HPLC chromatogram of this extracted cyanogen bromide-cleavage mixture is shown in FIG. 3A. The identity of each peptide peak was determined by mass spectrometry.

The reaction mixture yielded 77% αI13-HSl and 4% αI13-HS. Thus, 81% of the peptide mixture remained in the correct form of the peptide however, 9% dimerized to form (αI13-HSl)$_2$. The exact linkage between the two αI13HS peptides is not known but the molecular mass was correct for (αI13-HSl)$_2$. Incomplete cyanogen bromide cleavage was ruled out since that would have yielded peptide dimer that was 21 mass units heavier (HS versus Met). The most likely intrapeptide linkage formed between the C-terminal lactone of one αI13HSl peptide and its C-terminal partner is via the N-terminal Cα-NH$_2$ group because this primary amino group is more nucleophilic than the Lys-ε-NH$_2$ group on the α-Factor peptide.

Each α-Factor peptide HPLC peak was collected and ultraviolet absorption spectra obtained (FIG. 3) in order to confirm the aromatic amino acid composition and to provide a reliable method to determine purity and peptide concentration of all three species. Since each α-Factor peptide contained 1 Tyr:2 Trp, the expected extinction coefficient was $\epsilon_{279.4}$=12,300 M$^{-1}$cm$^{-1}$ based on the additive spectral contributions of the three aromatic amino acids (Kuliopulos et al, *Biochemistry*, 28:149–159 (1989)). This value agreed within 30% of the value based on the weight of the lyophilized peptide which was probably an underestimate because the dried peptide was a trifluoroacetate salt. The final yield of pure recombinant αI13-HS 14 amino acid was 56 mg/L of *E. coli*.

The KSIFIXQSMH$_6$ fusion protein which eventually yielded the FIXQS-HS 60 amino acid peptide, was also overproduced. Again, a majority of the KSIFIXQSMH$_6$ fusion protein was processed into inclusion bodies (FIG. 2), however, since the FIXQS sequence is quite hydrophilic (Kuliopulos, et al., *Biochemistry*, 31:9436–9444 (1992)) a sizable portion (40%) of the KSIFIXQSMH$_6$ fusion protein remained with the soluble protein fraction. The KSIFIX-QSMH$_6$ fusion was designed to have the C-terminal His$_6$ tag clipped off by cyanogen bromide from the rest of the FIXQS peptide after Ni-chelation chromatography, much in the way of the KSIαF$_n$H$_6$ fusion (compare FIG. 1A and 1C). Thus, the FIXQS(HS) peptide was first purified to homogeneity by Ni-chelate chromatography and then cleaved with cyanogen bromide to release the free FIXQS(HS) 60 amino acid peptide.

The strategy for extraction of the highly water soluble FIXQS(HS) peptide from the cyanogen bromide cleavage mixture differed from the extraction of the more hydrophobic αI13HS 14 amino acid. The FIXQS(HS) was either extracted with phosphate-buffered saline or by solubilization with 6M guanidine-HCl and subsequently dialyzed against high salt leaving behind the insoluble KSI peptides. The final yield of pure recombinant FIXQS-HS 60 amino acid was 50 mg/L of *E. coli*.

Figure 3B:
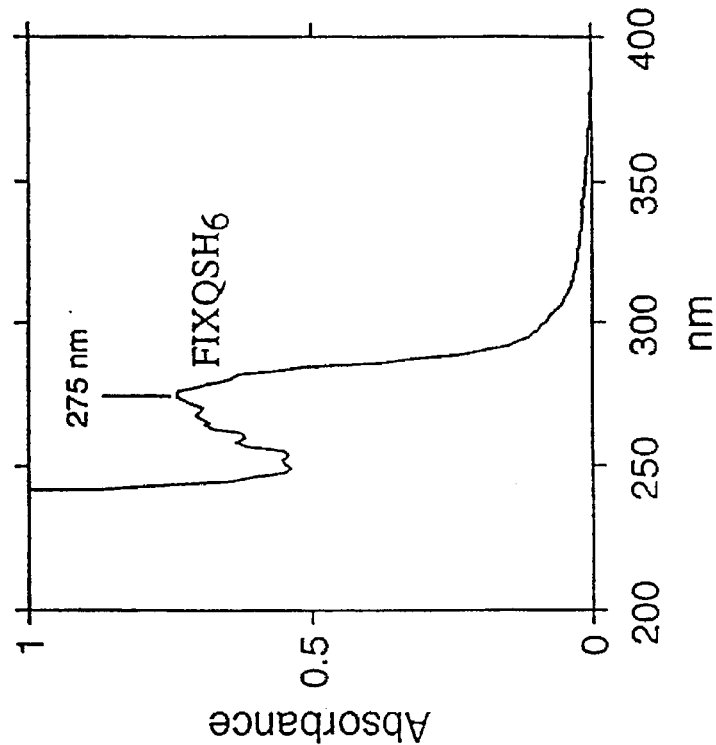
Figure 3B:
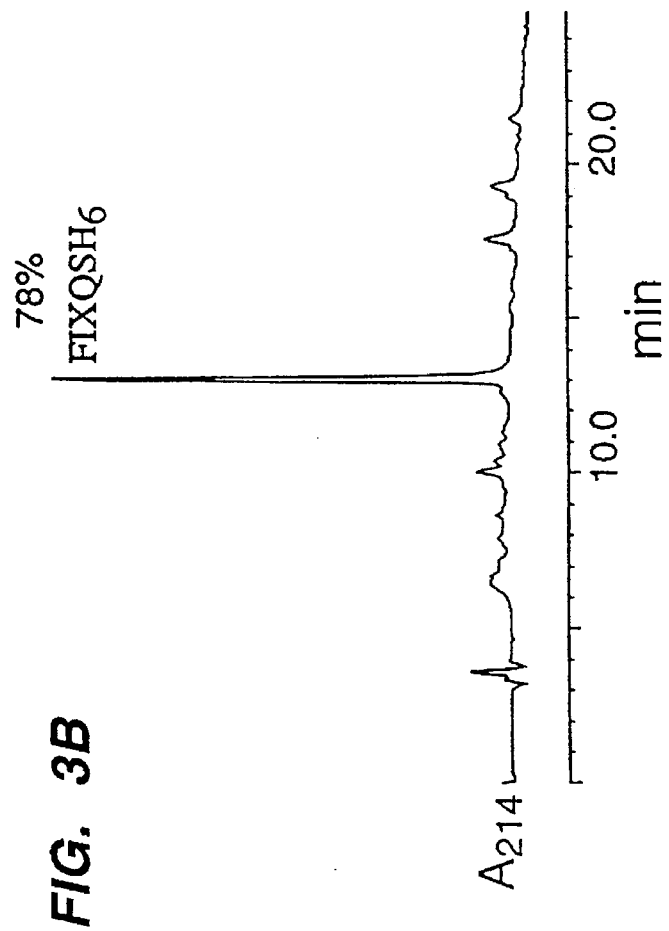

The longest recombinant peptide to be produced in this expression system was the FIXQSH$_6$ 67 amino acid peptide. As before, the KSIFIXQSH$_6$ fusion protein was overproduced and processed into inclusion bodies (Table 1). Since this peptide was designed to retain its C-terminal His$_6$ tag, no junctional Met residue was inserted before the His$_6$ cassette (FIG. 1D). Unlike the first two purification protocols, the KSIFIXQSH$_6$ fusion protein was cleaved by cyanogen bromide prior to Ni-chelate chromatography. The Ni-chelate affinity purified peptide was shown to be 78% pure by HPLC and ultraviolet absorption spectroscopy was performed as above (FIG. 3B). The aromatic absorption spectrum was quite different from the α-factor peptide and was quite typical for a polypeptide containing 1 Tyr: 5 Phe giving a major peak at 275 nm from Tyr ($\epsilon_{275}$1400 M$^{-1}$cm$^{-1}$) and 4 minor absorption maxima at 251, 257, 263, and 267 nm corresponding to phenylalanine fine structure (Kuliopulos, et al, *Biochemistry*, 28:149–159 (1989)). The final yield of pure recombinant FIXQSH$_6$ 67 amino acid was 55 mg/L of *E. coli*.

Example 4

Synthesis of peptide-homoserine lactone-conjugates.

The cleavage of methionine-containing peptides with cyanogen bromide will generate a C-terminal homoserine-lactone residue which can be used to create a plethora of peptide-HS-conjugates. Due to the unique reactivity of HS-lactone electrophile one should be able to couple a large number of primary-amine containing compounds to the C-terminus of any peptide-HS-lactone. The chemistries developed for C-terminal coupling of peptide-HS-lactones to amino glass resins used in solid-phase peptide sequencing have been adopted (Horn, and Laursen, *FEBS Letts.*, 36:285–288 (1973); Horn, *Anal. Biochem.*, 69:583–589 (1975)).

Figure 4:
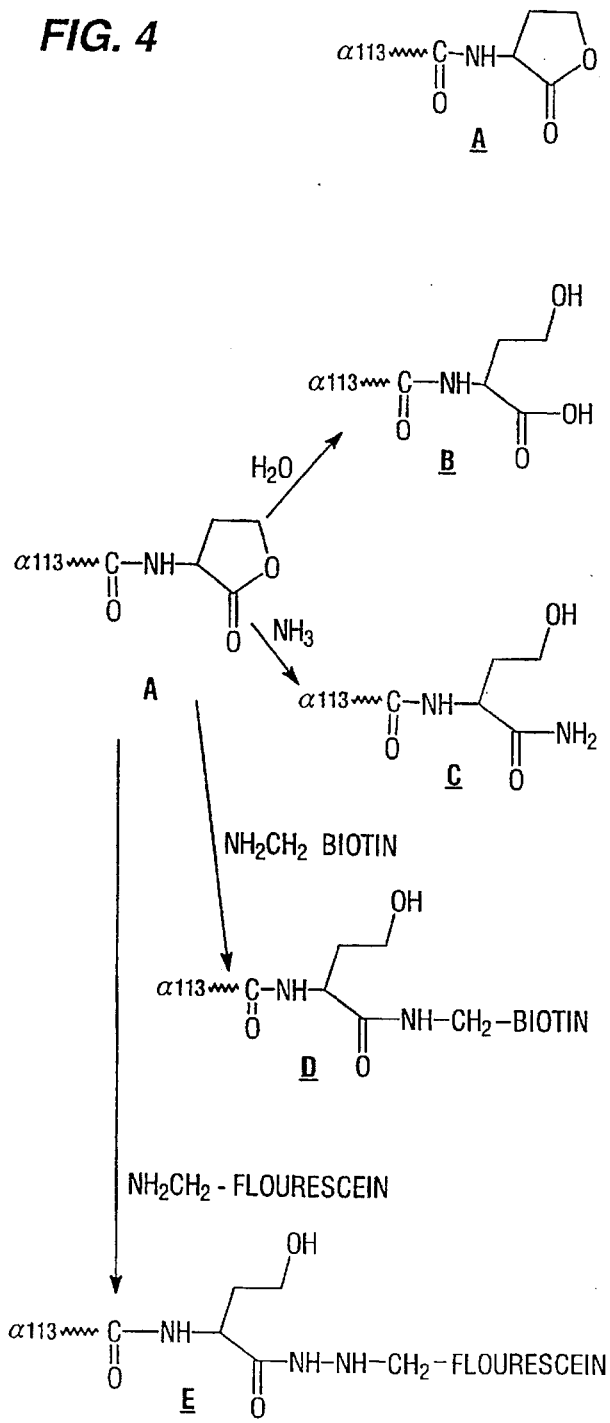
FIG. 4 depicts the synthetic scheme showing general routes to formation of recombinant α-Factor peptide-conjugates. The α-I13-homoserine-lactone was dissolved in anhydrous DMF and reacted with the indicated reagents in the presence of ET₃N. HPLC chromatograms of each of the reaction mixtures are shown on the right. The large peak eluting at 5–6 min in the bottom three traces is DMF. The masses (MH⁺) of the peptide conjugates were determined by FAB-MS. A is α-I13-HS-lactone; B is α-I13-HS; C is α-I13-HS-amid; D is α-I13-HS-biotin; and E is α-I13-HS-fluorescein.
Figure 4:
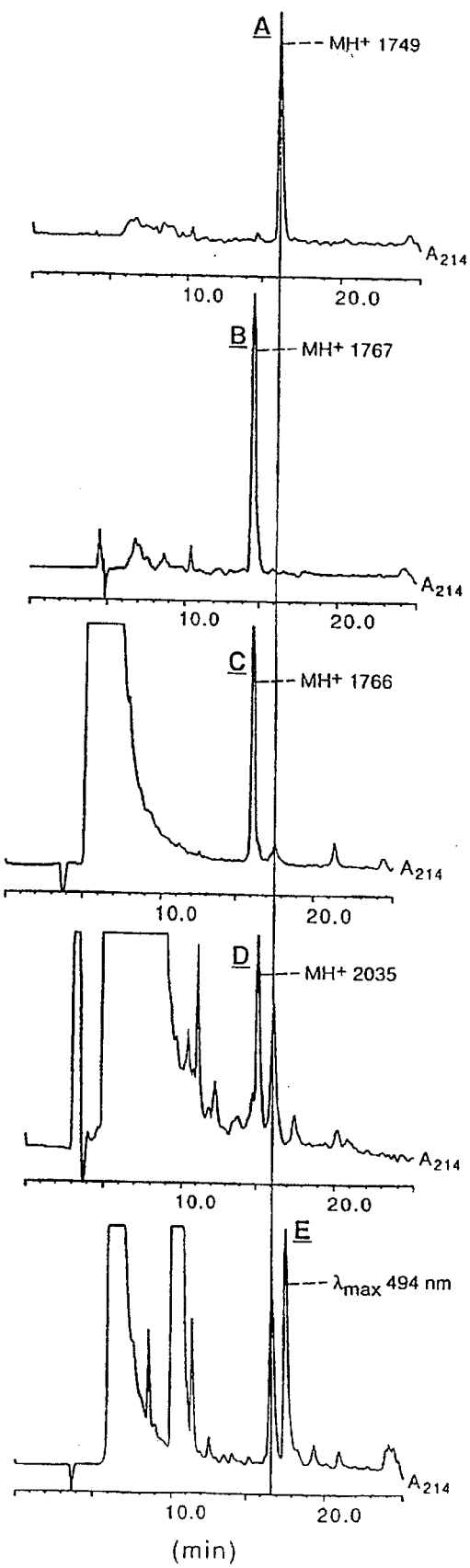

As shown in FIG. 4, the αI13-HSl was hydrolyzed or ammonolyzed to form the αI13-HS (B) and αI13-HS-amide (αI13-HSA, C), respectively. The HPLC chromatograms of these two reaction mixtures show the nearly complete conversion of the αI13-HSl to the correct products as confirmed by mass spectrometry. More complex αI13-HS-conjugates were also made using the DMF/Et$_3$N coupling system including the biotinylated- (D) and fluoresceinated- (E) peptides. A number of other recombinant peptide-HS-conjugates were also synthesized and their physical properties are shown in Table 2.

As shown in FIG. 4, the αI13-homoserine-lactone (αI13HSl) was dissolved in anhydrous DMF and reacted with the indicated reagents in the presence of Et$_3$N. Incubation temperatures and times for each reaction are listed herein. HPLC chromatograms of each of the reaction mixtures are shown on the right. HPLC conditions are the same as described in the FIG. 3 legend. The large peak eluting at 5-6 min in the bottom three traces is DMF. The masses (MH$^+$) of the peptide-conjugates were determined by FAB-MS except for E where the absorption maxima is indicated. A-αI13-HS-lactone; B-αI13-HS; C-αI13-HS-amide; D-αI13-HS-biotin; E-αI13-HS-fluorescein.

The yield of each of the coupling reactions depended largely on the solubility and steric bulk of the attacking group, however, at least a 50% yield was obtained in each case. Hydrazine-containing compounds were unreactive as nucleophiles with the αI13-HSl under the conditions employed.

Since longer, more hydrophilic peptides often are not soluble in DMF, the present invention provides an alternative coupling method which takes place under aqueous conditions. The present invention further provides peptide affinity columns which were attached to a resin solely at the C-terminus in order to leave the N-terminal region of the peptide free in mobile phase. Recombinant peptide affinity columns based on the FIXQS peptide are used to purify the membrane-bound vitamin K dependent carboxylase from eukaryotic sources (Wu et al., *Proc. Natl. Acad. Sci. USA*, 88:2236–2240 (1991); Kuliopulos, et al., *Biochemistry*, 31:9436–9444 (1992)). The FIXQS peptide contains 5 ε-amino groups and 1 C-terminal α-amino group and will randomly couple at multiple sites to the N-hydroxysuccinimide activated ester of an Affigel-10 resin. Previously made Affigel-10-peptide affinity columns were therefore potentially blocked at the critical N-terminal binding region of the FIXQS propeptide (residues −18, −17, −16, −15, and −10), or "γ-CRS recognition site".

The FIXQS-HSl 60 amino acid peptide was coupled to an amino alkyl Sepharose resin at pH 6 in NaOAc buffer although the coupling reaction required 170 hours to attain a 93% yield. The resulting FIXQS-HS-NH-Sepharose peptide affinity column was used to purify vitamin K dependent carboxylase ca. 3000-fold from crude bovine liver microsomes using established affinity purification procedures (Kuliopulos, et al., *Biochemistry*, 31:9436–9444 (1992)). The C-terminally tethered 60 amino acid peptide affinity column gave a 25% improvement in binding capacity relative to the randomly coupled FIXQS(HS)-Affigel-10 peptide affinity column. This selective coupling method employing the uniquely reactive C-terminal HS-lactone thus provides an alternative strategy for peptide affinity chromatography.

Example 5

Biological activity of recombinant α-Factor peptides.

The mature wild-type α-Factor peptide is a 13 amino acid pheromone secreted by type MATa yeast cells, which upon binding to the α-Factor receptor transmits a signal to an internally located G-protein. Once activated, this G protein triggers a series of intracellular events which lead to cellular differentiation (Elion et al., *Cell*, 60:649–664 (1990)). In the presence of external α-Factor, yeast cells in the early G$_1$ phase of growth will undergo cell cycle arrest. The bioactivity of each recombinant α-Factor could easily be determined in halo assays as a region of low cell density surrounding a central disk spotted with α-Factor (FIG. 5).

Lawns of yeast MATa/sst1Δ strain EY957 were grown on YPD plates and were tested for α-Factor sensitivity as previously described (Elion et al., *Cell*, 60:649–664 (1990)). α-Factor peptides were dissolved in DMSO and spotted on sterile 6.5 mm paper disks. Peptide amounts were as follows: Wild-type α-Factor (αFWT)-595 pmoles; αI13-homoserine-lactone (αI13-HSl)-6,850 pmoles; αI13-homoserine (αI13-HS)-1,130 pmoles; αI13-homoserine-amide (αI13-HSA)-2,820 pmoles. The zones of inhibition (z.o.i.) for each peptide is the diameter of the low cell density region.

Prior to constructing the tandem recombinant α-Factor gene which lacked the wild-type Met at position 12, we first synthesized and tested α-Factor peptides which had this internal Met changed to both Ile and Leu. The Cell Arrest$_{50}$ values (CA$_{50}$) and maximal zones of inhibition (z.o.i$_{int}$) of both αI13 and αL13 were essentially identical with those of wild-type (αFWT) α-Factor (Table 2). Thus we proceeded to construct the tandem recombinant α-Factor peptide with an Ile at position 12. The C-terminal HS-free acid form of the recombinant peptide, αI13HS, was shown to have the highest bioactivity. Its CA$_{50}$ value was 128% of the wild-type value and its z.o.i$_{int}$ value was ⅔ of wild-type.

The amidation of the C-terminal HS lactone, αI13HSA, resulted in a >11-fold increase in CA$_{50}$ indicating that a negative charge at the C-terminus is important for binding of these C-terminally extended α-Factor analogs. An additional C-terminal extension of the amide to either the ethylenediamine (αI13HS-ED) or ethanolamine (αI13HS-EO) derivatives completely abolished binding to the α-Factor receptor.

The lactone form of the recombinant α-Factor (αI13HSl), however, had a 2-fold higher CA$_{50}$ value relative to αFWT and its z.o.i$_{int}$ was ⅓ of αFWT also consistent with the C-terminus requiring a free carboxylate to bind the receptor. None of the larger αI13HS-conjugates had any appreciable agonist activity (Table 2) nor did they antagonize αFWT in dual disk competition assays (Eriotou-Bargiota et al., *Biochemistry*, 31:551–557 (1992)). These data would agree with the evidence that the C-terminal portion of the α-Factor is critical for receptor binding (Eriotou-Bargiota et al., *Biochemistry*, 31:551–557 (1992)).

Example 6

Construction of recombinant steroid isomerase-α-factor$_n$-His$_6$ genes

The procedure used to create the tandem repeat of the 14 codons of α-factor fused to the C-terminus of the 125 codons for the bacterial ketosteroid isomerase (KSI) gene (Kuliopulos et al., *Proc. Natl. Acad. Sci. USA*, 84:8893–8897 (1987)) is shown in FIG. 1A. The sense and anti-sense 42 amino acid deoxyoligonucleotide strands encoding the yeast α-factor peptide were designed using the preferred codon usage of *E. coli* (de Boer, and Kastelein, in *Maximizing Gene Expression* pp. 225–285, Butterworths (1986)). Each strand included a 3-base overhang for unidirectional end-to-end self ligation of the duplex 42 amino acids. 200 mg of each 42 amino acid peptide was purified on a 12.5% preparative denaturing polyacrylamide gel and desalted by passage through a C$_{18}$-SepPak (Millipore part No. WAT051910). 25 mg of each complementary strand was annealed and phosphorylated by incubation of the two strands for 1 hr at 37° C. in the presence of 125 units T4 polynucleotide kinase (New England Biolabs), 1 mM ATP, in a total volume of 100 μL.

After extraction with phenol and precipitation with ethanol, the 5'-phosphorylated duplex DNA was intermolecularly ligated at 8° C. for 16 hours using 15 units T4 DNA ligase (Boehringer catalogue No. 799009) in a total volume of 22 μL. An additional 10 units of T4 DNA ligase and 1 mM ATP was added after 18 hr and the reaction was allowed to proceed for another 24 hr at 8° C. The tandem DNA multimers were separated on a 3% low melting-point agarose gel and purified individual bands were used for the construction of the array of tandem-α-factor genes in pET22KSIHis$_6$.

The KSI gene from pAK808KSIY14F was inserted into the HindIII/BamHI sites of M13mp18 which served as the template by the mutagenesis procedure of Kunkel using the primer

5'-CTAGAAGGAGATATACATATGAATACCCCAGAA CACATGACC-3' (SEQ. ID NO: 2)

as previously described (Kuliopulos et al., *Biochemistry*, 31:9436–9444 (1992)). This introduced new Nde I and Nsi I sites, destroyed an old Nde I site, and created an additional mutation (N2H) at the 5' end of the KSI gene. This new KSI gene (N2H/Y14F) had an additional Xho I site placed at the 3' end of the gene by PCR mutagenesis using the (–) PCR primer

5'-GGAATTCCTCGAGCATAAATTCACTTGTCTTT TC-3'. (SEQ. ID. NO: 3)

This KSI gene was inserted into the Nde I/Xho I sites of pET22b (Novagen catalogue No. 69744-1) which was further digested with AlwN I and the ends were made blunt by incubation with Klenow (Boehringer catalogue No. 104523) and the 4 dNTP's.

The resulting blunt ends were ligated, thus destroying the AlwN I site at position 3634 to create pET22KSIΔAlwN I. The methionine at codon 7 was changed to isoleucine by PCR using the (+) PCR primer

5'-ATACATATGCATACCCCAGAACACATCACCGCC GTGG-3' (SEQ. ID NO: 4)

and the (–) PCR primer

5'-GTGGTGCTCGAGTCGCAGCATCTGGCCAGCGT GAAT-3' (SEQ. ID NO: 5)

was used to create an AlwN I site at the 3' end of the KSI gene. The PCR amplified product was inserted into the Nsi I/Xho I sites of pET22KSIΔAlwN I to create the universal tandem gene expression vector pET22KSIH$_6$ (FIG. 1B).

This expression vector was digested with AlwN I, dephosphorylated with calf intestinal alkaline phosphatase (New England Biolabs), and ligated at 8° C. for 16 hr with each different size tandem DNA multimer in separate reactions to create an array of pET22KSI(αF)$_n$H$_6$ constructs. The ligated DNA was transformed into DH5αFIQ and the number (n) of α-factor encoding 42 amino acid units of the resulting clones was ascertained by agarose gel electrophoresis. The appropriate constructs were then transformed into BL21(DE3) pLysS for protein overproduction. All fusion genes were sequenced to verify the number of tandem αF units and also to rule out adventitious mutations.

Example 7

Construction of recombinant steroid isomerase-FIXQS-His$_6$ genes

PCR mutagenesis was used to shuttle the previously constructed KSIFIX fusion gene from pAK808FIXQS (Kuliopulos et al., *Biochemistry*, 31:9436–9444 (1992)) into the pET22b expression vector. The (+) PCR primer used in the construction of both pET22KFMH (encodes FIXQS, FIG. 1C) and pET22KFH (encodes FIXQSH$_6$, FIG. 1D) was used previously to make pAK808FIXQS. The (–) PCR primers

5'-GGAATTCCTCGAGCATAAATTCAGTTGTCTTT TC-3' (SEQ. ID NO: 6)

and

5'-GGAATTCCTCGAGAAATTCAGTTGTCTTTTC-3' (SEQ. ID NO: 7)

were used to make pET22KFMH and pET22KFH, respectively. The PCR amplified products were ligated into the Nco I/EcoR I sites of pAK808KSIFIX (N2H/Y14F). The KFMH and KFH genes were subsequently ligated into the Nde I/Xho I sites of pET22b to make the final expression vectors pET22KFMH and pET22KFH. These constructs were then transformed into BL21(DE3)pLysS for protein overproduction.

Expression of KSIαF$_n$H$_6$, KSIFIXQS, and KSIFIXQSH$_6$ is described below. The fusion proteins were produced in the pET22b vector under the control of the T7lac promoter which is comprised of the T7 RNA polymerase promoter, the lac operator, and the lac repressor gene sequence in tandem. Studier, *J. Mol. Biol.*, 219:37–44 (1991). The protease deficient strain BL21(DE3)pLysS was used for all protein production. 25 mL cultures of cells were grown overnight in LB media containing 50 mg Ampicillin/L at 37° C. This starter culture was diluted 40-fold into 1-L of fresh LB-Amp and the cells induced with 1 mM IPTG when an absorbance of 0.3–0.5 at 595 nm was attained.

The cells were harvested at O.D. values of ca. 2.0 which was generally reached 3–6 hr after induction. The cell paste (2.5 g/L of *E. coli*) could be stored at –20° C. for at least a week without any loss in yield of fusion protein. The cell pellets were resuspended in 5 mM imidazole, 20 mM Tris-Cl, pH 7.9, 100 mM NaCl (5 mM Im-BB), sonicated, and centrifuged at 12,000× g for 10 min at 4° C. Levels of the total cellular protein, soluble protein, and insoluble protein were assessed by densitometry SDS-polyacrylamide gels stained with Coomassie blue R-250.

Example 8

His$_6$-Ni chelation affinity chromatography and cyanogen bromide cleavage of the fusion proteins The following 3 protocols are based on a 2-L culture of *E. coli*. All steps were performed at room temperature unless otherwise noted.

Protocol 1

Production and Purification of Recombinant Tandem α-Factor 14 Amino Acids

The insoluble cellular protein pellet contains the majority of the fusion protein as dense inclusion bodies. This wet pellet (3.8 g) was dissolved in 45 mL of 5 mM Im-BB/6M guanidine-HCl (5 mM Im-BB/6G). This mixture was recentrifuged at 12,000× g, 10 min, 4° C. to remove particulate matter. The supernatant was loaded onto a 50-mL Ni-imino diacetic acid column (His-Bind resin/Novagen catalogue No. 69670-2) which had been charged with NiSO$_4$ and equilibrated with 5 mM Im-BB/6G at a flow rate of 2.5 mL/min. The column was washed with 150 mL of 5 mM Im-BB/6G and then with 200 mL of 16 mM Im-BB/6G. The fusion protein was eluted with 150 mL of 300 mM Im-BB/6G. The protein in each fraction was assessed for purity on 10–15% SDS-PAGE PHAST gels (Pharmacia). The peak fractions were combined (96 mL), dialyzed overnight at 4° C. against 2×10 L of H$_2$O in 12–14 kDa molecular weight cut-off (MWCO) dialysis bags. The majority of the protein formed a white precipitate which could be pelleted by centrifugation at 2000× g for 10 min at 4° C.

The dense white pellet (5 g) was resolubilized in 60 mL of 80% formic acid, transferred to a 250 mL round-bottomed flask and 2 g of cyanogen bromide added. Nitrogen was bubbled in, the flask was wrapped in aluminum foil and stirred for 18–22 hours. This reaction mixture was rotoevaporated to dryness in 90 min at 28° C. The resultant transparent proteinaceous gel that formed was resuspended in 20 mL 40% $CH_3CN$/60% $H_2O$/0.1 % TFA and stirred for 1 hr. This suspension was centrifuged at 12,000× g for 10 min at 4° C. The supernatant was further clarified by passage through a 0.22 μm filter and the purity of the recombinant α-factor-HS(lactone) analyzed by reverse-phase HPLC and UV spectroscopy. The protein concentration was determined using a $\epsilon_{279.4}$ value of 12,300 $M^{-1}cm^{-1}$.

Protocol 2

Production and Purification of Recombinant FIXQS 60 Amino Acid

The purification and cyanogen bromide cleavage of the FIXQS peptide from the KSIFIXQSMH$_6$ fusion protein was the same as in Protocol 1 until the cyanogen bromide cleavage step. Here the two protocols diverged due to the differing solubility between the very hydrophilic 60 amino acid and the hydrophobic 14 amino acid α-factor. After the cyanogen bromide cleaved peptide mixture was dried by rotoevaporation, the gelatinous material was resuspended in 20 mM $KPO_4$, 100 mM NaCl, and the pH adjusted to 7.4 with 1M $NaHCO_3$. This mixture was stirred overnight under $N_2$ and wrapped in aluminum foil. The suspension was centrifuged at 5000× g for 15 min at 4° C. and the supernatant analyzed by UV spectroscopy. The 60 amino acid in the supernatant was either concentrated by rotoevaporation or dried by lyophilization. The pellet contained ca. 50% of the FIXQS-HS(lactone) which could be extracted with 5 mM Im-BB/6G and dialyzed overnight against 500 mM NaCl in dialysis bags of 3350 MWCO (Spectrum part 132724) at 4° C. This dialysate was centrifuged and the supernatant analyzed as before.

Protocol 3

Production and Purification of Recombinant FIXQSH$_6$ 67 Amino Acid

The production of this recombinant peptide from the KSIFIXQSH$_6$ fusion protein was different than the other two peptides because the His$_6$ tag was designed to remain attached to the peptide after cyanogen bromide cleavage at the junctional methionine between the KSI carrier protein and the C-terminal FIXQSH$_6$ peptide. The inclusion body-containing insoluble cell pellets were directly dissolved in 80% formic acid, cleaved with cyanogen bromide, and dried by rotoevaporation as in Protocol 1. The resulting gelatinous material was resolubilized in a minimal volume of 6.5M guanidine-HCl and transferred to 3350 MWCO dialysis bags. This material was dialyzed overnight at 4° C. against 20 mM Tris-HCl, pH 8.1, 50 mM NaCl. The dialysate was centrifuged at 12,000× g, for 15 min at 4° C. and the supernatant filtered through a 0.22 μm filter. The supernatant was loaded onto a Ni chelation affinity column equilibrated with 5 mM Im-BB. Note that unlike the other two protocols, no guanidine-HCl was used during this affinity purification. The column was sequentially washed with 5 mM Im-BB and 30 mM Im-BB, and eluted with 300 mM Im-BB. The protein concentration of both FIXQSH$_6$ and FIXQS-HS(lactone) was determined by the method of Goodwin and Morton. See Kuliopulos et al., *Biochemistry*, 31:9436–9444 (1992).

Example 9

Synthesis of recombinant α-factor peptide conjugates

Recombinant αI13-homoserine-lactone (αI13-HSl) produced by Protocol 1 was purified to >99% purity by reverse phase HPLC and lyophilized to a fluffy white powder. The peptide was stable at −20° C. for at least 6 months without degradation or loss of biological activity. The lactone could be completely and immediately converted to the free acid form of homoserine (αI13-HS) by addition of 0.2N NaOH. For each of the following reactions, 0.3–0.8 mg (170–460 nmoles) of αI13-HS-lactone were placed in 1.7-mL polypropylene tubes and completely lactonized by addition of 20 μL of 100% TFA and immediately dried in a SpeedVac (Savant model SVC-100H1).

The dried pellets were dissolved in 50 μL anhydrous DMF delivered by a gas-tight syringe and 8 μL of Et$_3$N was added. All reaction tubes were equipped with a micro-stirbar. Synthesis of αI13-HSA: 50 μL of anhydrous DMF saturated with $NH_3$ gas was added directly to the dried lactonized pellet prior to the addition of Et$_3$N. This reaction was stirred at 44° C. and amidation was complete in 30 min. Synthesis of αI13-HS-ED: 25 equivalents of ethylenediamine were added to the lactonized peptide solution and the reaction was complete after 68 min at 45° C. Synthesis of αI13-HS-EO: 250 equivalents of ethanolamine were added to the lactonized peptide solution and the reaction was complete in 68 min at 45° C. Synthesis of αI13-HS-biotin: 100 equivalents of biotin ethylenediamine (Molecular Probes catalogue #A-1593) were added to the lactonized peptide solution and the reaction allowed to proceed for 5 hr 12 min at 48° C. Synthesis of αI13-HS-fluorescein: 28 equivalents of fluoresceinyl glycine amide (Molecular Probes catalogue #A-1363) were dissolved in an additional 100 μL DMF and added to the lactonized peptide solution and the reaction was allowed to proceed for 7 hr 45 min at 48° C. Synthesis of αI13-HS-dansyl: 37 equivalents of dansyl ethylenediamine (Molecular Probes catalogue #D-112) were added to the lactonized peptide solution and the reaction was allowed to proceed for 7 hr 10 min at 48° C. Synthesis of αI13-HS-ANS: 100 equivalents of 5((2-aminoethyl)amino) naphthalene-1-sulfonic acid (Molecular Probes catalogue #A-91) were dissolved in an additional 200 μL DMF plus an additional 32 μL Et$_3$N and added to the lactonized peptide solution and the reaction was allowed to proceed for 5 hr 50 min at 45° C.

All syntheses of recombinant α-factor peptide conjugates were monitored by RP-HPLC. Peak fractions were collected and their compositions and concentrations determined by UV spectroscopy. The compositions of each recombinant peptide-conjugate was also verified by both laser desorption mass spectrometry and by FAB mass spectrometry as already described (Kuliopulos et al., 1992).

Example 10

Aqueous coupling of recombinant FIXQS-HS-lactone to aminoalkyl sepharose.

The recombinant 60 amino acid FIXQS-HS-lactone was purified as described in Protocol 2. Four mg of lyophilized FIXQS-HS-lactone was placed into a 1.7-mL polypropylene tube and solubilized with 765 μL 0.88M NaOAc, and the pH was adjusted to 6 with NaOH. 0.5 mL of aminoalkyl Sepharose (Affigel 102 -Pharmacia) was added and the mixture was gently rocked for 170 hr at 37° C. The extent of the coupling was monitored by removing small aliquots at various time points and determining the amount of peptide remaining in the supernatant by the Bradford Method.

Example 11

Yeast cell arrest assays

HPLC purified recombinant α-factor-HS, α-factor-HS-conjugates, and synthetic α-factors were dissolved in DMSO at concentrations of 1 mg/mL. A 10-fold diluted stock solution was also made for each peptide in 60% H$_2$O/40% CH$_3$CN/0.1% TFA. Wild-type α-factor was from Sigma and αI13 and αL13 were synthesized by standard fmoc solid phase chemistry. The EY957 yeast strain (MATa/sst1Δ) was kindly provided by E. Elion at the Harvard Medical School. The cell arrest assays were performed according to Elion et al., *Cell*, 60:649–664 (1990) except that 100 μL of an overnight culture of EY957 was used instead of 50 μL.

TABLE 1

Production of Recombinant KSI-Peptide His$_6$ Fusion Proteins[a].

| KSI-peptide His$_6$ | peptide monomer length (a.a.) | KSI-peptide-length (a.a.) | total KSI-peptide MW (da) | % peptide KSI-peptide (da/da) | % [KSI-peptide] [tot. cell prot.] (μg/μg)[b] | % [KSI-peptide] [tot. insol. prot.] (μg/μg/)[b] | max yield of peptide[c] (mg/L) | Actual yield of pure peptide[d] (mg/L) |
|---|---|---|---|---|---|---|---|---|
| KSI-αF$_0$-H$_6$ | 0 | 136 | 14,918 | 0 | 74 | 70 | 0 | |
| KSI-αF$_1$-H$_6$ | 14 | 150 | 16,678 | 10.7 | 76 | 72 | 24 ± 8 | |
| KSI-αF$_3$-H$_6$ | 14 | 178 | 20,234 | 26.3 | 65 | 74 | 57 ± 19 | |
| KSI-αF$_5$-H$_6$ | 14 | 206 | 23,790 | 37.3 | 68 | 65 | 72 ± 24 | 56 |
| KSI-αF$_6$-H$_6$ | 14 | 220 | 25,568 | 41.7 | 58 | 55 | 69 ± 23 | |
| KSIFIXQSMH$_6$ | 60 | 194 | 21,596 | 32.6 | 67 | 65 | 48 ± 16 | 50 |
| KSIFIXQSH$_6$ | 67 | 193 | 21,465 | 37.1 | 67 | 58 | 66 ± 22 | 55 |

[a]Fusion genes were expressed in the protease deficient strain BL21(DE3)pLysS. Overnight cultures were diluted 40-fold and induced with 1 mM IPIG at A$_{595}$ = 0.3–0.5 OD. Cells were harvested 6 hours after induction. Sonicated cells were centrifuged in order to pellet insoluble cellular proteins and inclusion bodies. Total cellular protein, insoluble protein, and soluble protein fractions were analyzed by SDS-PAGE and densitometry.
[b]Determined by the Bradford Method using IgG as a standard.
[c]Obtained from (peptide/KSI-peptide) × ([KSI-peptide]/[tot. insol. prot.]) × (300 mg/L). The toal insoluble protein (300 ± 100 mg/L) was obtained from 14 separate measurements of sonicated insoluble material from cells harvested 6 hours after induction with 1 mM IPTG.
[d]KSI-peptide-His$_6$ fusion protein was purified from the inclusion body pellets, purified by Ni-chelate chromatography, cleaved with Cyanogen bromide, and purified by HPLC according to Protocols 1–3 as described in Example 8.

TABLE II

Physical Properties and Biological Activity of Recombinant Yeast Alpha-Factor Peptide-Conjugates.

| peptide | structure | MH$^{+a}$ (m/z) | yield[b] (%) | z.o.i.$_{int}$[c] (mm) | CA$_{50}$[d] (pmoles) |
|---|---|---|---|---|---|
| Synthetic Peptides | | | | | |
| αFWT | WHWLQLKPGQPMY | 1687[e] | | 29 ± 3 | 74 ± 5 |
| αI13 | WHWLQLKPGQPIY | 1666[e] | | 27 ± 1 | 84 ± 33 |
| αL13 | WHWLQLKPGQPLY | 1666[e] | | 26 ± 2 | 91 ± 40 |
| Recombinant Peptides | | | | | |
| αI13-HS1 | αI13—C(=O)—NH—[homoserine lactone] | 1749[f] | | 11 ± 3 | 170 ± 27 |
| αI13-HS | αI13—C(=O)—NH—[homoserine, OH] | 1767[f] | 97 | 18 ± 3 | 95 ± 37 |
| αI13-HSA | αI13—C(=O)—NH—[homoserine amide, NH$_2$] | 1766[f] | >88 | | >830 |
| αI13-HS1$_2$[g] | αI13—C(=O)—NH—[homoserine]—NH-αI13—C(=O)—NH—[homoserine lactone] | 3500[e] | | | |

TABLE II-continued

Physical Properties and Biological Activity of Recombinant Yeast Alpha-Factor Peptide-Conjugates.

| peptide | structure | MH+a (m/z) | yieldb (%) | z.o.i.intc (mm) | CA50d (pmoles) |
|---|---|---|---|---|---|
| αI13-HSED | 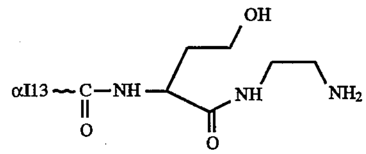 | 1813e | >90 | | no effect at 5,500 pmoles |
| αI13-HSEO | 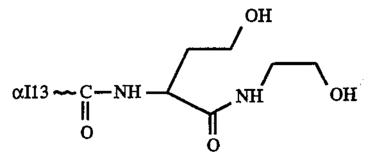 | 1814e | >90 | | no effect at 5,500 pmoles |
| αI13-HS-Biotin | 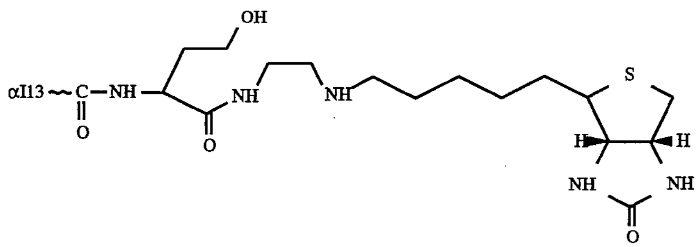 | 2035f | 58 | | >950 |
| αI13-HS-Fluoresceinh | | | 56 | | no effect at 6,700 pmoles |
| αI13-HS-Dansyl | 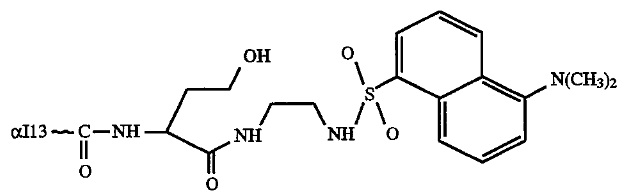 | 2042f | 50 | | no effect at 4,900 pmoles |
| αI13-HS-ANS | | 2017e | 51 | | no effect at 740 pmoles | aThe molecular ion (MH+) of each HPLC purified peptide peak was determined by FAB-MS or by Laser Desorption-MS as indicated. In each case, the observed MH+ mass agreed to within 1 Da of the calculated mass.
bDetermined by integration of HPLC traces at 214 nm of reaction mixtures described in the Methods section.
cThe zone of inhibition in mm (z.o.i.) was measured for each series of different concentration α-factor and plotted against amount (pmoles) of α-factor spotted per disk. The sigmoidal curves that were generated had three regions including a horizontal line drawn through 6.5 mm (the diameter of the disk), the sigmoidal portion of the curve, and an upper asymptope which always had a positive slope. The y-intercept of this asymptope (z.o. $i_{int}$) obtained for each α-factor peptide served as a reliable measure of the relative maximal effects of each α-factor peptide in the cell arrest assay.
dThe cell arrest50 (CA50) values in pmoles were calculated by drawing a tangent through the inflection point of the sigmoidal portion of the curve and obtaining the point of intersection with the upper asymptope. This value was divided by 2 and 3.25 mm added to obtain the z.o.i. value at which 50% of the maximal effect is seen (CA50) or the amount of peptide required to cause 50% of cell arrest under the conditions employed.

TABLE II-continued

Physical Properties and Biological Activity of Recombinant Yeast Alpha-Factor Peptide-Conjugates.

| peptide | structure | MH[+a] (m/z) | yield[b] (%) | z.o.i.[c]_int (mm) | CA_50[d] (pmoles) |
|---|---|---|---|---|---|

[e] Determined by Laser Desorption mass spectrometry.
[f] Determined by FAB mass spectrometry.
[g] Formed spontaneously during the CNBr cleavage reactions. Although the most likely structure is drawn, alternative amide bond linkages (i.e. via the Lys-ε-NH$_2$) could form with the C-terminal lactone and still have the molecular mass as shown.
[h] The FAB-MS for this compound gave no peak and the Laser Desorption-MS analysis was not reliable, however, the HPLC-purified compound, E. shown in FIG. 4 had the expected UV-Vis absorption characteristics of a fluorescein-peptide derivative with a maximal absorption occurring at 494.3 nm in 60% H$_2$O/40% CH$_3$CN/0.5% Et$_3$N, pH 10. The authentic fluorescein-glycine-amide starting material had a nearly identical absorption spectra and maximally absorbed at 497.6 nm under the same conditions.

While the present invention has been described in conjunction with the preferred embodiments and illustrative examples, one of ordinary skill after reading the foregoing specification will be able to affect various changes, substitution of equivalents and other alterations to the invention provided herein. It is therefore intended that the protection granted by letters patent hereon be limited only by the definitions contained in the appended claims and equivalents thereof. It will be understood that changes may be made in the details of formulation without departing from the spirit of the invention as defined in the following claims.

---

We claim:

1. A vector comprising:
nucleic acid encoding a carrier peptide and, at the 3' end of said nucleic acid a unidirectional restriction endonuclease cleavage site, recognized by a restriction endonuclease with the ability to create a non-palindromic 3-base overhang, wherein said 3-base overhang is a 3' ATG overhang.

2. The vector of claim 1, wherein said vector further comprises a T7 lac promoter located on the 5' end of said carrier peptide.

3. The vector of claim 1, wherein said carrier peptide is insoluble and comprises the first 125 amino acids of the ketosteroid isomerase gene.

4. The vector of claim 1, wherein said restriction endonuclease is AlwNI.

5. A vector comprising:
nucleic acid encoding a carrier peptide and, at the 3' end of said nucleic acid a unidirectional restriction endonuclease cleavage site, recognized by a restriction endonuclease with the ability to create a non-palindromic 3-base overhang; wherein said restriction endonuclease is AlwNI.

6. The vector of claim 5, wherein said vector further comprises a T7 lac promoter located on the 5' end of said carrier peptide.

7. The vector of claim 5, wherein said carrier peptide is insoluble and comprises the first 125 amino acids of the ketosteroid isomerase gene.

8. The vector of claim 5, wherein said 3-base overhang is a 3' ATG overhang.

9. A vector comprising nucleic acid encoding a recombinant fusion peptide having at least part of a ketosteroid isomerase gene linked to one or more desired peptides and a $His_6$ tag attached to a C-terminal desired peptide, wherein each said desired peptide is separated from another by a single amino acid.

10. The vector of claim 9, wherein said part of a ketosteroid isomerase gene is the first 125 amino acids of the ketosteroid isomerase gene.

11. The vector of claim 9, wherein said vector further comprises a T7 lac promoter on the 5' end of the nucleic acid encoding said recombinant fusion peptide and part of a ketosteroid isomerase gene.

12. The vector of claim 9, wherein said amino acid is methionine.

13. The vector of claim 9, wherein said desired peptide is α-Factor or FIXQS.

14. A vector comprising:
nucleic acid encoding a carrier peptide and, at the 3' end of said nucleic acid a unidirectional restriction endonuclease cleavage site, recognized by a restriction endonuclease with the ability to create an in-frame non-palindromic 3-base overhang.

15. A method for producing a fusion peptide comprising the steps of:
(a) providing a vector comprising nucleic acid encoding a carrier peptide and, at the 3' end of said nucleic acid, a unidirectional restriction endonuclease cleavage site recognized by a restriction endonuclease with the ability to create a non-palindromic 3-base overhang;
(b) cleaving said vector with said restriction endonuclease to produce a cleaved vector;
(c) ligating to said site one or more linear nucleic acids encoding a desired peptide having at least a 3-base overhang at each end configured and arranged for ligation with said cleaved vector to produce a second vector;
(d) transforming said second vector into suitable host cell; and
(e) incubating said host cell under condition suitable for expression of said fusion peptide;
wherein said second vector encodes a recombinant fusion peptide having said carrier peptide linked to one or more said desired peptides, wherein each said desired peptide is separated from another by a single amino acid encoded by said 3-base overhang; and wherein said 3-base overhang is a 3' ATG overhang.

16. The method of claim 15, wherein said method is performed in *Escherichia coli*.

17. The method of claim 16, wherein said *Escherichia coli* is protease deficient.

18. The method of claim 17, wherein said protease deficient *Escherichia coli* is strain BL21(DE3)pLysS.

19. The method of claim 15, wherein said vector further comprises a T7 lac promoter located on the 5' end of said carrier peptide.

20. The method of claim 15, wherein said carrier peptide is insoluble and comprises the first 125 amino acids of the ketosteroid isomerase gene.

21. A method for producing a fusion peptide comprising the steps of:
  (a) providing a vector comprising nucleic acid encoding a carrier peptide and, at the 3' end of said nucleic acid, a unidirectional restriction endonuclease cleavage site recognized by a restriction endonuclease with the ability to create a non-palindromic 3-base overhang;
  (b) cleaving said vector with said restriction endonuclease to produce a cleaved vector;
  (c) ligating to said site one or more linear nucleic acids encoding a desired peptide having at least a 3-base overhang at each end configured and arranged for ligation with said cleaved vector to produce a second vector;
  (d) transforming said second vector into suitable host cell; and
  (e) incubating said host cell under condition suitable for expression of said fusion peptide;
  wherein said second vector encodes a recombinant fusion peptide having said carrier peptide linked to one or more said desired peptides, wherein each said desired peptide is separated from another by a single amino acid encoded by said 3-base overhang; and wherein said restriction endonuclease is AlwNI.

22. The method of claim 21, wherein said desired peptide is α-factor or FIXQS.

23. The method of claim 21, wherein said ligation is performed in a single step.

24. The method of claim 21, wherein said desired peptide is produced in yields equal to or greater than 5 mg/L of *Escherichia coli*.

25. The method of claim 25, wherein said desired peptide is produced in yields equal to or greater than 25 mg/L of *Escherichia coli*.

26. The method of claim 25, wherein said desired peptide is produced in yields equal to or greater than 50 mg/L of *Escherichia coli*.

27. The method of claim 21, further comprising the steps of:
  (a) attaching a C-terminal $His_6$ peptide tag to said fusion peptide;
  (b) separating said fusion peptide from other peptides in a host cell by Ni-chelate chromatography; and
  (c) cleaving said fusion peptide at each said single amino acid releasing said carrier peptide, said tag, and said desired peptide or peptides.

28. The method of claim 27, wherein said cleaving comprises cleaving with any specific enzyme or chemical agent.

29. The method of claim 27, wherein said single amino acid is methionine and wherein said cleaving comprises cleaving with cyanogen bromide.

30. The method of claim 27, wherein said single amino acid is tryptophan and wherein said cleaving comprises cleaving with O-iodosobenzoic acid.

31. A method for producing a fusion peptide comprising the steps of:
  (a) providing a vector comprising nucleic acid encoding a carrier peptide and, at the 3' end of said nucleic acid, a unidirectional restriction endonuclease cleavage site recognized by a restriction endonuclease with the ability to create an in-frame non-palindromic 3-base overhang;
  (b) cleaving said vector with said restriction endonuclease to produce a cleaved vector; and
  (c) ligating to said site one or more linear nucleic acids encoding a desired peptide having at least a 3-base overhang at each end configured and arranged for ligation with said cleaved vector to produce a second vector;
  (d) transforming said second vector into suitable host cell; and
  (e) incubating said host cell under condition suitable for expression of said fusion peptide;
  wherein said second vector encodes a recombinant fusion peptide having said carrier peptide linked to one or more said desired peptides, wherein each said desired peptide is separated from another by a single amino acid encoded by said 3-base overhang.

32. The method of claim 31, wherein said method is performed in *Escherichia coli*.

33. The method of claim 32, wherein said *Escherichia coli* is protease deficient.

34. The method of claim 33, wherein said protease deficient *Escherichia coli* is strain BL21(DE3)pLysS.

35. The method of claim 31, wherein said vector further comprises a T7 lac promoter located on the 5' end of said carrier peptide.

36. The method of claim 31, wherein said carrier peptide is insoluble and comprises the first 125 amino acids of the ketosteroid isomerase gene.

37. The method of claim 31, wherein said desired peptide is α-factor or FIXQS.

38. The method of claim 31, wherein said ligation is performed in a single step.

39. The method of claim 31, wherein said desired peptide is produced in yields equal to or greater than 5 mg/L of *Escherichia coli*.

40. The method of claim 39, wherein said desired peptide is produced in yields equal to or greater than 25 mg/L of *Escherichia coli*.

41. The method of claim 40, wherein said desired peptide is produced in yields equal to or greater than 50 mg/L of *Escherichia coli*.

42. The method of claim 31, further comprising the steps of:
  (a) attaching a C-terminal $His_6$ peptide tag to said fusion peptide;
  (b) separating said fusion peptide from other peptides in a host cell by Ni-chelate chromatography; and
  (c) cleaving said fusion peptide at each said single amino acid releasing said carrier peptide, said tag, and said desired peptide or peptides.

43. The method of claim 42, wherein said cleaving further comprises cleaving with any specific enzyme or chemical agent.

44. The method of claim 42, wherein said single amino acid is methionine or tryptophan and wherein said cleaving comprises cleaving with cyanogen bromide or O-iodosobenzoic acid.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 9
        ( B ) TYPE: nucleic acid
        ( C ) STRANDEDNESS: single
        ( D ) TOPOLOGY: linear ( x i ) SEQUENCE DESCRIPTION: SEQ ID NO: 1:
        C A G N N N C T G        9

( 2 ) INFORMATION FOR SEQ ID NO: 2:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( x i ) SEQUENCE DESCRIPTION: SEQ ID NO: 2:
        C T A G A A G G A G  A T A T A C A T A T  G A A T A C C C C A  G A A C A C A T G A  C C    4 2

( 2 ) INFORMATION FOR SEQ ID NO: 3:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 3:
        G G A A T T C C T C  G A G C A T A A A T  T C A C T T G T C T  T T T C    3 4

( 2 ) INFORMATION FOR SEQ ID NO: 4:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 4:
        A T A C A T A T G C  A T A C C C C A G A  A C A C A T C A C C  G C C G T G G    3 7

( 2 ) INFORMATION FOR SEQ ID NO: 5:

```
( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 5:
             GTGGTGCTCG  AGTCGCAGCA  TCTGGCCAGC  GTGAAT                36

( 2 ) INFORMATION FOR SEQ ID NO: 6:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 6:
             GGAATTCCTC  GAGCATAAAT  TCAGTTGTCT  TTTC                  34

( 2 ) INFORMATION FOR SEQ ID NO: 7:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 7:
             GGAATTCCTC  GAGAAATTCA  GTTGTCTTTT  C                     31
```